(12) United States Patent
Deutsch

(10) Patent No.: US 7,405,071 B2
(45) Date of Patent: Jul. 29, 2008

(54) METHOD AND DEVICE FOR MANIPULATING INDIVIDUAL SMALL OBJECTS

(75) Inventor: Mordechai Deutsch, Doar-Na Lev HaSharon (IL)

(73) Assignee: Seng Enterprises Ltd., Larnaca (CY)

( * ) Notice: Subject to any disclaimer, the term of this patent is extended or adjusted under 35 U.S.C. 154(b) by 323 days.

(21) Appl. No.: 10/546,784

(22) PCT Filed: Feb. 26, 2004

(86) PCT No.: PCT/IL2004/000194

§ 371 (c)(1),
(2), (4) Date: Aug. 25, 2005

(87) PCT Pub. No.: WO2004/077009

PCT Pub. Date: Sep. 10, 2004

(65) Prior Publication Data

US 2006/0154233 A1 Jul. 13, 2006

Related U.S. Application Data

(60) Provisional application No. 60/496,382, filed on Aug. 20, 2003, provisional application No. 60/496,383, filed on Aug. 20, 2003, provisional application No. 60/523,094, filed on Nov. 19, 2003, provisional application No. 60/523,096, filed on Nov. 19, 2003.

(30) Foreign Application Priority Data

Feb. 27, 2003 (IL) .................................... 154677

(51) Int. Cl.
*C12M 1/36* (2006.01)
(52) U.S. Cl. ........................... 435/286.2; 435/4; 435/5; 435/287.2; 435/289.1; 435/440

(58) Field of Classification Search ................... 435/4, 435/5, 286.2, 287.2, 289.1, 440
See application file for complete search history.

(56) References Cited

U.S. PATENT DOCUMENTS

| 4,308,351 A | 12/1981 | Leighton et al. |
| 4,729,949 A | 3/1988 | Weinreb et al. |

(Continued)

FOREIGN PATENT DOCUMENTS

| EP | 1566635 | 8/2005 |

(Continued)

OTHER PUBLICATIONS

Yamamura et al. "Single-Cell Microarray for Analyzing Cellular Response", Analytical Chemistry, 77(24): 8050-8056, 2005.

(Continued)

*Primary Examiner*—Walter D. Griffin
*Assistant Examiner*—Shanta G Doe

(57) ABSTRACT

A method for individually moving small objects, such as cells, from one location to another as well as a device for implementing the method is disclosed. A small object such as a cell is isolated at some initial location and moved to some destination location by the movement of the small object through a succession of intermediate locations until the small object arrives at the destination location. Also disclosed are methods of manipulating cells made possible by the method and device of the present invention.

23 Claims, 25 Drawing Sheets

U.S. PATENT DOCUMENTS

| | | | |
|---|---|---|---|
| 4,894,343 | A | 1/1990 | Tanaka et al. |
| 5,059,266 | A | 10/1991 | Yamane et al. |
| 5,204,055 | A | 4/1993 | Sachs et al. |
| 5,272,081 | A | 12/1993 | Weinreb |
| 5,395,588 | A | 3/1995 | North, Jr. et al. |
| 5,428,451 | A | 6/1995 | Lea et al. |
| 5,506,141 | A | 4/1996 | Weinreb et al. |
| 5,627,045 | A | 5/1997 | Bochner et al. |
| 5,650,323 | A | 7/1997 | Root et al. |
| 5,707,869 | A | 1/1998 | Wolf et al. |
| 5,854,684 | A | 12/1998 | Stabile et al. |
| 5,905,031 | A | 5/1999 | Kuylen et al. |
| 6,046,426 | A | 4/2000 | Jeantette et al. |
| 6,066,285 | A | 5/2000 | Kumar |
| 6,103,479 | A | 8/2000 | Taylor |
| 6,117,612 | A | 9/2000 | Halloran et al. |
| 6,206,672 | B1 | 3/2001 | Grenda |
| 6,228,437 | B1 | 5/2001 | Schmidt |
| 6,238,614 | B1 | 5/2001 | Yang et al. |
| 6,329,195 | B1 | 12/2001 | Pfaller |
| 6,333,192 | B1 | 12/2001 | Petitte et al. |
| 6,338,964 | B1 | 1/2002 | Matanguihan et al. |
| 6,342,384 | B1 | 1/2002 | Chung et al. |
| 6,344,354 | B1 | 2/2002 | Webster et al. |
| 6,372,494 | B1 | 4/2002 | Naughton et al. |
| 6,376,148 | B1 | 4/2002 | Liu et al. |
| 6,377,721 | B1 | 4/2002 | Walt et al. |
| 6,378,527 | B1 | 4/2002 | Hungerford et al. |
| 6,383,810 | B2 | 5/2002 | Fike et al. |
| 6,403,369 | B1 | 6/2002 | Wood |
| 6,410,309 | B1 | 6/2002 | Barbera-Guillem et al. |
| 6,413,744 | B1 | 7/2002 | Morris et al. |
| 6,413,746 | B1 | 7/2002 | Field |
| 6,455,310 | B1 | 9/2002 | Barbera-Guillem et al. |
| 6,465,000 | B1 | 10/2002 | Kim |
| 6,465,205 | B2 | 10/2002 | Hicks, Jr. |
| 6,468,788 | B1 | 10/2002 | Marotzki |
| 6,479,252 | B1 | 11/2002 | Barbera-Guillem et al. |
| 6,485,690 | B1 * | 11/2002 | Pfost et al. .................. 422/102 |
| 6,489,144 | B1 | 12/2002 | Lau |
| 6,492,148 | B1 | 12/2002 | van Loon et al. |
| 6,492,163 | B1 | 12/2002 | Yoo et al. |
| 6,495,340 | B2 | 12/2002 | Huberman et al. |
| 6,506,598 | B1 | 1/2003 | Andersen et al. |
| 6,511,430 | B1 | 1/2003 | Sherar et al. |
| 6,528,286 | B1 | 3/2003 | Ryll |
| 6,544,788 | B2 | 4/2003 | Singh |
| 6,555,365 | B2 | 4/2003 | Barbera-Guillem et al. |
| 6,569,422 | B1 | 5/2003 | van Loon et al. |
| 6,588,586 | B2 | 7/2003 | Abasolo et al. |
| 6,589,765 | B1 | 7/2003 | Choi et al. |
| 6,593,140 | B1 | 7/2003 | Field |
| 6,610,516 | B1 | 8/2003 | Andersen et al. |
| 6,627,426 | B2 | 9/2003 | Biddle et al. |
| 6,632,619 | B1 | 10/2003 | Harrison et al. |
| 6,635,448 | B2 | 10/2003 | Bucciarelli et al. |
| 6,642,050 | B1 | 11/2003 | Goto et al. |
| 6,645,757 | B1 | 11/2003 | Okandan et al. |
| 6,649,408 | B2 | 11/2003 | Bailey et al. |
| 6,660,501 | B2 | 12/2003 | Field |
| 6,667,034 | B2 | 12/2003 | Palsson et al. |
| 6,670,180 | B2 | 12/2003 | Block |
| 6,670,184 | B2 | 12/2003 | Chiarello et al. |
| 6,673,591 | B2 | 1/2004 | Lau |
| 6,686,190 | B2 | 2/2004 | Lau |
| 6,689,594 | B1 | 2/2004 | Hänni et al. |
| 6,692,961 | B1 | 2/2004 | Judd et al. |
| 7,118,910 | B2 * | 10/2006 | Unger et al. ............. 435/288.5 |
| 7,169,578 | B2 * | 1/2007 | Wang et al. .................... 435/30 |
| 2002/0064885 | A1 * | 5/2002 | Bedingham et al. ......... 436/174 |
| 2002/0106715 | A1 | 8/2002 | Huberman et al. |
| 2002/0173033 | A1 | 11/2002 | Hammerick et al. |
| 2002/0189374 | A1 | 12/2002 | DeSilets et al. |
| 2003/0030184 | A1 | 2/2003 | Kim et al. |
| 2003/0032204 | A1 | 2/2003 | Walt et al. |
| 2003/0104494 | A1 | 6/2003 | Ravkin et al. |
| 2003/0124716 | A1 | 7/2003 | Hess et al. |
| 2003/0189850 | A1 | 10/2003 | Sasaki et al. |
| 2003/0211458 | A1 | 11/2003 | Sunray et al. |
| 2004/0235143 | A1 | 11/2004 | Sasaki et al. |
| 2005/0014201 | A1 | 1/2005 | Deutsch |
| 2005/0064524 | A1 | 3/2005 | Deutsch et al. |
| 2006/0057557 | A1 | 3/2006 | Deutsch et al. |

FOREIGN PATENT DOCUMENTS

| | | |
|---|---|---|
| JP | 2005-102628 | 4/2005 |
| WO | WO 98/15356 | 4/1998 |
| WO | WO 98/35223 | 8/1998 |
| WO | WO 99/45357 | 9/1999 |
| WO | WO 99/47922 | 9/1999 |
| WO | WO 01/35071 | 5/2001 |
| WO | WO 01/88176 | 11/2001 |
| WO | WO 02/26114 | 4/2002 |
| WO | WO 02/063034 | 8/2002 |
| WO | WO 03/035824 | 1/2003 |
| WO | WO 03/011451 | 2/2003 |
| WO | WO 03/056330 | 7/2003 |
| WO | WO 2004/113492 | 12/2004 |
| WO | WO 2005/007796 | 1/2005 |
| WO | WO 2005/069001 | 7/2005 |

OTHER PUBLICATIONS

Dolbeare "Fluorescent Staining of Enzymes for Flow Cytometry", Methods Cell Biol., 33(Chap.8): 81-88, 1990.

Klingel et al. "Flow Cytometric Determination of Serine Proteinase Activities in Living Cells With Rhodamine 110 Substrates", Methods Cell Biol., 41(Chap.29): 449-460, 1994.

Malin-Berdel et al. "Flow Cytometric Determination of Esterase and Phosphatase Activities and Kinetics in Hematopoietic Cells With Fluorogenic Substrates", Cytometry, 1(3): 222-228, 1980.

Nooter et al. "On-Line Flow Cytometry. A Versatile Method for Kinetic Measurement", Methods Cell Biol., 41(Chap.32): 509-526, 1994.

Turek et al. "Leucine Aminopeptidase Activity by Flow Cytometry", Methods Cell Biol., 41(Chap.30): 461-468, 1994.

Watson et al. "Enzyme Kinetics", Methods Cell Biol., 41: 469-508, 1994.

Bedner et al. "Enzyme Kinetic Reactions and Fluorochrome Uptake Rates Measured in Individual Cells by Laser Scanning Cytometry", Cytometry, 33(1): 1-9, 1998. Abstract, p. 2, col. 1, §4-col. 2, §1, p. 8, col. 2, §2.

Sunray et al. "Cell Activation Influences Cell Staining Kinetics", Spectrochimica Part A, 53: 1645-1653, 1997.

Eisenthal et al. "Infection of K562 Cells With Influenza A Virus Increases Their Susceptibility to Natural Killer Lysis", Pathobiology, 65: 331-340, 1997.

Deutsch et al. "Apparatus for High-Precision Repetitive Sequential Optical Measurement of Living Cells", Cytometry, 16: 214-226, 1994.

Sunray et al. "Determination of the Michaelis-Menten Constant (Km) of Intracellular Enzymatic Reaction for Individual Live Lymphocytes", Cytometry Supplement, 10: 68-69, & The XX Congress of the International Society for Analytical Cytology, Montpellier, F, 2000.

Darzynkiewicz et al. "Laser-Scanning Cytometry: A New Instrumentation With Many Applications", Experimental Cell Research, 249(1): 1-12, 1999. Abstract, p. 2, col. 2, §4-p. 4, col. 2, §2, p. 8, col. 1, §1-col. 2, §2.

Sunray et al. "The Trace and Subgrouping of Lymphocyte Activation by Dynamic Fluorescence Intensity and Polarization Measurements", Biochemical and Biophysical Research Communications, 261(3): 712-719, 1999. Abstract, p. 713, col. 1, §5, col. 2, §7—p. 714, col. 2, §1.

Sunray et al. "Determination of Individual Cell Michaelis-Menten Constants", Cytometry, 47(1): 8-16, 2002.

Dive et al. "Improved Methodology for Intracellular Enzyme Reaction and Inhibition Kinetics by Flow Cytometry", Cytometry Journal of Society for Analytical Cytology, 8(6): 552-561, 1987.

Koh et al. "Poly(Ethylene Glycol) Hydrogel Microstructures Encapsulating Living Cells", Langmuir, 18(7): 2459-2462, 2002. p. 2459-2462, Fig.3.

Lansing Taylor et al. "Real-Time Molecular and Cellular Analysis: The New Frontier of Drug Discovery", Current Opinion in Biotechnology, 12: 75-81, 2001.

Aplin et al. "Protein-Derivatised Glass Coverslips for the Study of Cell-to-Substratum Adhesion", Analytical Biochemistry, 113: 144-148, 1981.

Burlage et al. "Living Biosensors for the Management and Manipulation of Microbial Consortia", Annual. Rev. Microbiol., 48: 291-309, 1994.

Mrksich et al. "Using Self-Assembled Monolayers to Understand the Interactions of Man-Made Surfaces With Proteins and Cells", Annual Reviews in Biophysics and Biomolecular Structure, 25: 55-78, 1996.

Singhvi et al. "Engineering Cell Shape and Function", Science, 264: 696-698, 1994.

Riedel et al. "Arxula Adeninivorans Based Sensor for the Estimation of Bod", Analytical Letters, 31(1): 1-12, 1998.

Simonian et al. "Microbial Biosensors Based on Potentiometric Detection", Methods in Biotechnology,6, chapter 17: 237-248, 1998.

Arikawa et al. "Microbial Biosensors Based on Respiratory Inhibition", Methos in Biotehnology,6, chapter 16: 225-235, 1998.

* cited by examiner

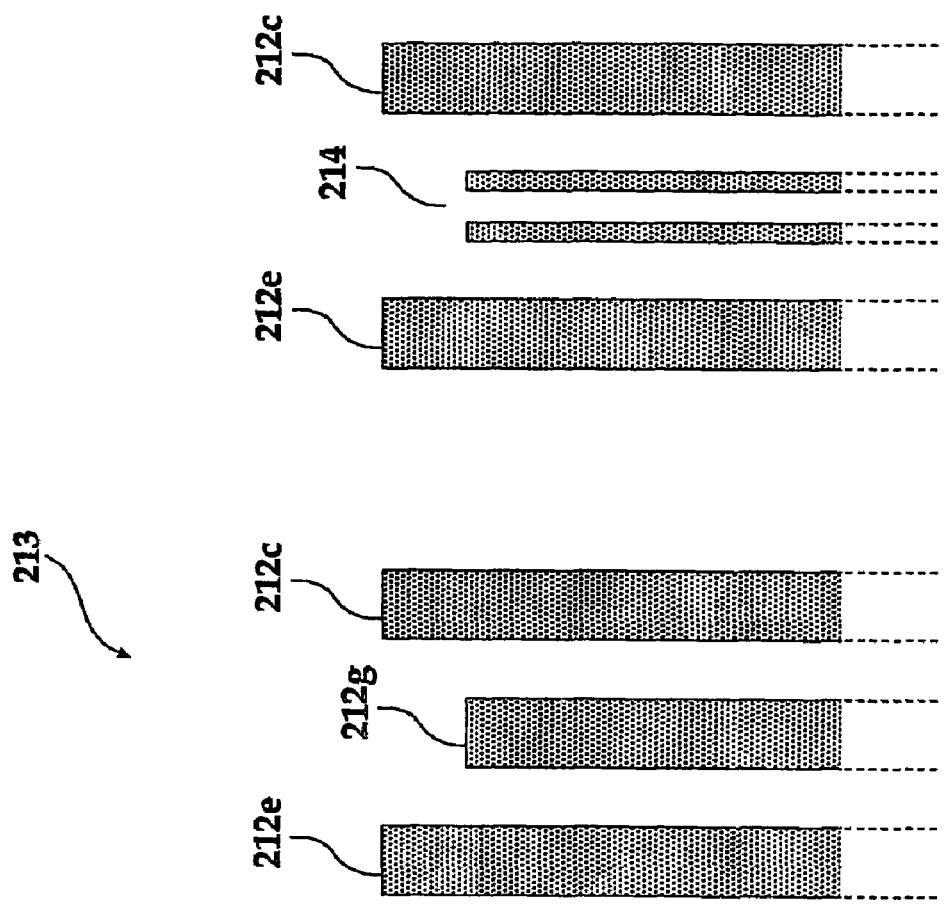
FIG.9C
FIG.9B
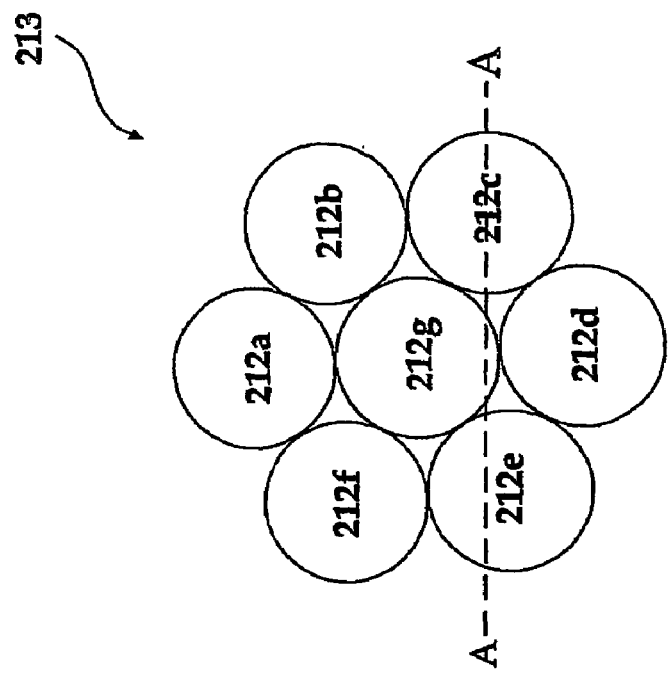
FIG.9A

METHOD AND DEVICE FOR MANIPULATING INDIVIDUAL SMALL OBJECTS

RELATED PATENT APPLICATION

This application is a National Phase Application of PCT/IL2004/000194 having International Filing Date of 26 Feb. 2004, which claims the benefit of Israel Patent Application No. 154677 filed 27 Feb. 2003, U.S. Provisional Patent Application No. 60/496,382 filed 20 Aug. 2003, U.S. Provisional Patent Application No. 60/496,383 filed 20 Aug. 2003, U.S. Provisional Patent Application No. 60/523,094 filed 19 Nov. 2003, U.S. Provisional Patent Application No. 60/523,096 filed 19 Nov. 2003. The contents of the above Application are all incorporated herein by reference.

FIELD AND BACKGROUND OF THE INVENTION

The present invention relates to the field of micromanipulation and, more particularly, to a method to and device for physically manipulating small objects, especially living cells. The present invention also relates to the field of life sciences, and more particularly to a device and methods for individually manipulating cells.

In the fields of biology and medicine it is often important to study the results of the interaction between living cells and external factors such as environment, physical stimuli, chemical stimuli and other cells. Such studies are important, for example, for medical diagnostics, drug development and the understanding of basic cell function and are generally divided into two types, static and dynamic studies.

In static studies a group of cells are exposed to whatever stimulus is being studied and, after a certain time, the magnitude and nature of the reaction of the group of cells to the stimulus are determined.

In dynamic studies a single cell or a group of cells is exposed to whatever stimulus is being studied and the magnitude and nature of the reaction of the cell or group to the stimulus are determined, either continuously or discretely.

Both static and dynamic studies are often performed on a population of cells on a macroscopic scale, in cuvettes or well arrays. One disadvantage of studying populations of cells is that the results may teach of secondary effects rather than primary effects of stimuli: the response of a cell to the response of other cells to a stimulus is detected rather than the effect of the stimulus itself. Another disadvantage of such studies is that the results reflect a distribution of effects on a group of cells. This disadvantage is partially overcome by the use of homogenous populations of cells. Although the study of homogenous populations of cells is informative, results are not necessarily representative of "real-life" effects. Although theoretically possible, the required manipulations using available technologies are too difficult and too slow when applied to the study of individual cells.

Static and dynamic studies are also performed using flow cytometry. In flow cytometry, the response of a cell to a stimulus is measured or detected for a single cells moving through a medium, the cell being discarded subsequently to the measurement. Flow-cytometry allows neither the study of an individual cell over a period of time nor the study of the interaction of two or more specifically selected cells.

Practitioners of flow cytometry realize that many critical questions in cell biology, developmental biology, immunology, oncology, pharmacology and virology cannot be answered using even the most sophisticated flow cytometry techniques. It is clear to one skilled in the art that complete understanding of complex biological problem requires the dynamic manipulation and study of single cells or of a multiplicity of cells studied as individuals in parallel or sequentially.

There is thus a widely recognized need for, and it would be highly advantageous to have, a method to manipulate, isolate and study single, whole, living cells as individuals.

SUMMARY OF THE INVENTION

The above needs are met by the present invention which allows isolation and manipulation of an individual small object such as a single cell.

The present invention successfully addresses the shortcomings of the prior art by providing a method for moving a small object (such as a cell) from one location to another location, thus allowing isolation and manipulation of the small object. The present invention also provides a device for implementing the method of the present invention.

According to the teachings of the present invention there is provided a method of moving an individual small object from an initial location to a destination location by:

a. defining a series of N+1 locations $L_0 \ldots L_N$, N being an integer greater than 1 wherein $L_0$ is the initial location and $L_N$ is the destination location; and b. for i from 0 to N−1, successively moving the individual small object from a location $L_i$ to a location $L_{i+1}$ wherein moving the small object is effected by applying an attractive force from location $L_{i+1}$ to the individual small object so as to cause the individual small object to move from location $L_i$ to location $L_{i+1}$.

According to an embodiment of the present invention, the position and/or orientation of location $L_i$ is fixed relative to the position and/or orientation of location $L_{i+1}$.

According to an embodiment of the present invention, to aid in moving the small object, a repulsive force is applied to the individual small object from location $L_i$ before, during or after application of the attractive force from location $L_{i+1}$.

According to a feature of the present invention, either or both an attractive force or a repulsive force can be physical, electrical and/or magnetic.

According to a preferred embodiment of the present invention, a repulsive force is a result of a flow of fluid from location $L_i$, preferably the flow of fluid being generated by injection of a fluid from the vicinity of location $L_i$.

According to a preferred embodiment of the present invention, an attractive force is a result of a flow of fluid towards location $L_{i+1}$, preferably the flow of fluid being generated by suction of a fluid from the vicinity of location $L_{i+1}$.

According to a feature of the present invention, at least one (and preferably all) of the locations $L_0 \ldots L_N$, includes an enclosure of a size sufficient to substantially enclose (partially or completely) the individual small object (and preferably no more than one small object at a time).

According to the teachings of the present invention there is also provided a method of moving an individual small object in a fluid from a first location to a second location by:

a. drawing fluid towards the first location so as to produce a first force localizing the small object at the first location; and b. subsequently drawing fluid towards the second location so as to produce a second force localizing the small object at the second location.

According to an embodiment of the present invention, the position and/or orientation of the first location is fixed relative to the position and/or orientation of the second location.

According to an embodiment of the present invention, the drawing of fluid towards the first location and the drawing of fluid towards the second location are performed by suction of the fluid by a flow generator. Suitable flow generators include, but are not limited to, one or more pumps, and systems that use valves and the like.

According to an embodiment of the present invention, before, during or after the drawing of fluid towards the second location, the magnitude of the first force is reduced so as to assist in localizing the small object at the second location.

According to an embodiment of the present invention, before, during or after the drawing of fluid towards the second location, the first force is eliminated so as to assist in localizing the small object at the second location.

According to an embodiment of the present invention, before, during or after the drawing of fluid towards the second location, fluid is injected from the first location so as to produce a repulsive force to assist in localizing the small object at the second location.

According to an embodiment of the present invention, the first location and the second location include an enclosure of a size sufficient to substantially enclose (partially or completely) the individual small object (and preferably no more than one small object at a time). In such an embodiment, the drawing of fluids towards the first location and towards the second location is preferably performed by suction of the fluids from within a respective enclosure.

Depending on the specific embodiment of the present invention, the size of individual small objects manipulated according to the teachings of the present invention include objects is in the order of equal to or less than about $10^3$ micron, equal to or less than about $10^2$ micron, equal to less than about $10^1$ micron or equal to less than about $10^0$ micron. Such objects include crystals, bacteria, viruses, proteins, polymers, macromolecules, ions and atoms, but especially cells.

In embodiments of the present invention using a fluid, it is preferred that the fluid is a liquid, preferably a cell culture medium.

According to the teachings of the present invention there is also provided a cell manipulation device, specifically configured to manipulate individual cells found in a liquid such as a cell culture medium. The cell manipulation device according to the teachings of the present invention includes:
  a. at least N locations; and
  b. at least two flow generators, each flow generator being functionally associated with a location;

wherein N is at least two;

wherein at least two of the flow generators are independently settable to a mode selected from the group of modes including a suction mode and an inactive mode; and wherein at least two of the independently settable flow generators are each associated with a different location. One embodiment of a device of the present invention has two locations, each one of the two locations having a functionally associated independently settable flow generator.

According to an embodiment of the present invention, the position and/or orientation of at least one of the N locations is fixed relative to the position and/or orientation of another one of the N locations. According to a preferred embodiment of the present invention, all of the at least N locations having a fixed relative position and/or orientation relative to the other locations.

According to an embodiment of the present invention, N is at least three and at least three of the at least N locations are arranged in a one-dimensional array. By one-dimensional array is meant that each one of the N locations is adjacent to no more than two other locations.

According to an embodiment of the present invention, N is at least four and at least four of the at least four locations are arranged in a two-dimensional array. By two-dimensional array is meant that at least one of the N locations is adjacent to more than two other locations.

According to an embodiment of the present invention, N is at least five and at least five of the at least five locations are arranged in a rectangular lattice array. By rectangular lattice array is meant that at least one of the N location is adjacent to four other locations. Preferably, substantially all "non-border" locations are adjacent to four other locations.

According to an embodiment of the present invention, N is at least seven and at least seven of the at least seven locations are arranged in a hexagonal lattice array. By hexagonal lattice array is meant that at least one of the N location is adjacent to six other locations. Preferably, substantially all "non-border" locations are adjacent to six other locations.

According to various embodiments of the present invention, N is at least ten, 19, 24, 36 and even more.

According to an embodiment of the present invention, at least one of the flow generators is independently settable to a mode selected from the group of modes including a suction mode, an injection mode and an inactive mode. Preferably, substantially all of the flow generators are independently settable to a mode selected from the group of modes including a suction mode, an injection mode and an inactive mode.

According to an embodiment of the present invention, at least one of the N locations is associated with at least two flow generators and each one of these at least two flow generators is independently settable to a mode selected from the group of modes including a suction mode and an inactive mode (and preferably a suction mode, an injection mode and an inactive mode).

According to an embodiment of the present invention, at least one of the N locations is associated with at least three flow generators and each one of these at least three flow generators is independently settable to a mode selected from the group of modes including a suction mode and an inactive mode (and preferably a suction mode, an injection mode and an inactive mode).

According to an embodiment of the present invention, at least two of the at least N locations are substantially defined by the presence of an inlet of a respective flow-generator.

According to an embodiment of the present invention, at least two of the at least N locations are substantially depressions in a surface.

According to an embodiment of the present invention, at least two of the at least N locations are substantially open trapping-ends of enclosures. Each such enclosure is of a size sufficient to substantially enclose (partially or completely) a cell (and preferably no more than one cell). According to a preferred embodiment, within at least two of the at least two enclosures emerges an inlet of a respective flow generator. The device of the present invention is specifically configured to manipulate cells. Accordingly, the size of open trapping ends of enclosures is of a size sufficient to allow entry of a cell to be studied, and preferably only one such cell at a time. Accordingly, according to embodiments of the present invention, the order of the size of the open trapping ends are equal to or less than about $10^3$ micron, equal to or less than about $10^2$ micron, equal to or less than about $10^1$ micron and/or equal to or less than about $10^0$ micron.

According to an embodiment of the present invention, to allow for efficient transfer of cells between one location and another location (in accordance with the method of the present invention), at least one location is no more than 1000 micron distant from at least one other location, preferably substantially every location being no more than 1000 micron distant from at least one other location.

According to an embodiment of the present invention, to allow for efficient transfer of cells between one location and another location (in accordance with the method of the present invention), at least one location is no more than 100 micron distant from at least one other location, preferably substantially every location being no more than 100 micron distant from at least one other location.

According to an embodiment of the present invention, to allow for efficient transfer of cells between one location and another location (in accordance with the method of the present invention), at least one location is no more than 10 micron distant from at least one other location, preferably substantially every location being no more than 10 micron distant from at least one other location.

According to an embodiment of the present invention, to allow for efficient transfer of cells between one location and another location (in accordance with the method of the present invention), at least one location is no more than 1 micron distant from at least one other location, preferably substantially every location being no more than 1 micron distant from at least one other location.

According to an embodiment of the present invention, at least one of the locations is configured so as to suspend a cell at distance above itself using a Venturi effect, as explained hereinbelow in detail.

According to an embodiment of the present invention, at least one of the locations is provided with a cell wall penetrating tool. According to a feature of the present invention, each such cell wall penetrating tool is a member (including but not limited to needles, wires and sharpened protuberances) pointing in a direction substantially opposite a flow generated by a flow generator functionally associated with the location when set to a suction mode. As will be described hereinbelow in detail, when the flow generator is set to a suction mode, a cell is pulled towards and onto the cell wall penetrating tool with sufficient force to effect cell wall penetration.

According to the teachings of the present invention there is also provided a method of studying a cell by suspending the cell individually in a liquid by using a Venturi effect.

According to the teachings of the present invention there is provided a device for suspending a cell in a liquid including: a. a substantially hollow body having an open trapping-end and a central axis; b. emerging within the hollow body, at least one outlet of a flow generator configured to inject liquid into the hollow body and through the open trapping-end in a first flow substantially parallel to the central axis of the hollow body; and c. emerging within the hollow body, at least one inlet of a flow generator configured to draw liquid through the open trapping-end and out of the hollow body in a second flow substantially parallel to the central axis of the hollow body; wherein the first flow is closer to the central axis than the second flow. Such a cell suspension device can be integrated into the cell manipulation device of the present invention, where the hollow body defines, in part, a location or enclosure as described hereinabove.

According to the teachings of the present invention there is also provided a method of penetrating a cell wall by: a. immersing, in a liquid, a cell wall penetrating tool pointing in a first direction; and b. applying suction from a second direction opposite the first direction so as to cause a cell in the liquid to be carried against the cell wall penetrating tool where the intensity of the carrying is sufficient to cause a wall of the cell to be penetrated.

According to the teachings of the present invention there is also provided a device for penetrating a cell wall including a. a substantially hollow body having an open trapping-end; b. emerging within the hollow body, at least one inlet of a flow generator configured to draw liquid out of the hollow body in a flow having a first direction; and c. a cell wall penetrating tool pointing in a second direction substantially opposite the first direction. Such a cell wall penetrating device can be integrated into the cell manipulation device of the present invention, where the hollow body defines, in part, a location or enclosure as described hereinabove.

According to the teachings of the present invention there is also provided a method for selecting cells by: a. providing a group of cells; b. isolating cells from the group of cells in an individual enclosure; c. examining each isolated cell; and d. selecting isolated cells fulfilling at least one criterion. According to a feature of the present invention, the selected cells are separated from the group of cells.

According to the teachings of the present invention there is also provided a method for treating a cell-containing biological fluid by a. providing the cell-containing biological fluid; b. identifying cells to be treated in the biological fluid; c. differentiating between cells to be treated and other cells; and d. either or both:
  i. physically separating the cells to be treated from the other cells; and/or
  ii. directly manipulating the cells to be treated thus treating the biological fluid.

According to a feature of the present invention, during the identifying, each cell is isolated in an individual enclosure.

Examples of direct manipulation of the cells to be treated includes but is not limited to destroying the cells to be treated (e.g., physically, chemically, irradiation), exposing the cells to be treated to a reagent (e.g. internally or externally, chemical reagents, biological reagents), exposing the cells to be treated to radiative energy (e.g. ultraviolet, infrared, visible light, coherent light, incoherent light, microwaves) and penetrating the cell walls of the cells to be treated (e.g. to inoculate the cells or to remove a sample from therewithin).

Examples of treatable biological liquids include but are not limited to lymphatic fluids, blood, cerebral spinal fluids, semen, saliva, synovial fluid, bone marrow, cochlear fluid, fluid extracted from tumors, ovarian fluid, amniotic fluid and chorionic fluid.

According to an embodiment of the present invention, subsequent to d, the biological liquid is directed into a living organism (both human and non-human).

According to an embodiment of the present invention, providing the biological liquid includes a step of taking the biological liquid from a living organism (both human and non-human).

According to an embodiment of the present invention, e. subsequently to d, the biological liquid is directed into a living organism (both human and non-human) and providing the biological liquid includes a step of directing the biological liquid to flow from the living organism to the individual enclosures.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the patent specification, including definitions, will control. In addition, the materials, methods, embodiments and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a multiplicity of software instructions being executed by a computer using any suitable operating system. In any case, selected steps of the method and system of the invention could be described as being performed by a data processor, such as a computing platform for executing a multiplicity of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 9A-9C illustrate a method of producing a cell manipulation element from glass tubes and rods;

DETAILED DESCRIPTION OF THE INVENTION

Figure 1C:
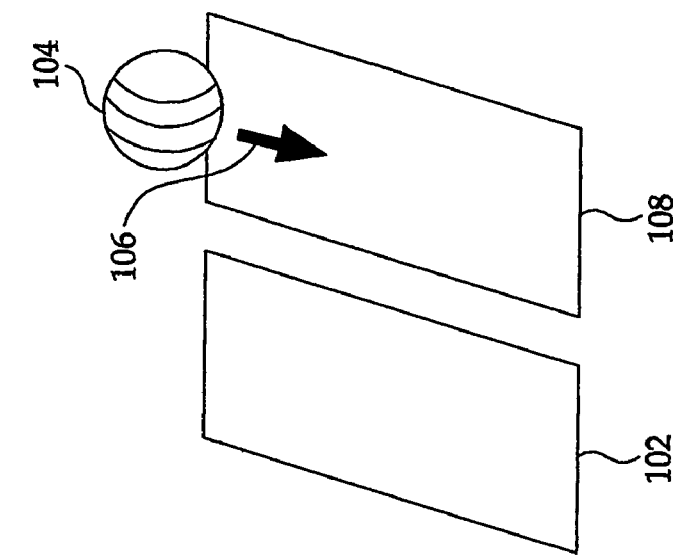
FIGS. 1A-1C illustrate the method of the present invention for moving a small object from one location to a neighboring location using only attractive forces.

The present invention is of a method and a device that allow the isolation and manipulation of individual small objects, such as and especially living cells. With the appropriate modifications, some embodiments of present invention allow the practitioner to isolate, manipulate, observe and study an individual small object such as a living. cell. By manipulate is meant to physically move but especially to expose to many different and well-defined stimuli, including but not limited to chemical and physical stimuli. Using the teachings of the present invention, complex multi-step experiments can be reproducibly performed on single individual small objects such as living cells.

The principles and operation of a device and method of the present invention may be better understood with reference to the drawings and accompanying descriptions.

Before explaining at least one embodiment of the invention in detail, it is to be understood that the device of the present invention is not limited in its application to the details of construction and the arrangement of the components set forth in the following description or illustrated in the drawings. It is also to be understood that the method of the invention is not limited in its application to the details set forth in the following description or exemplified by the specific embodiments. The invention is capable of other embodiments or of being practiced or carried out in various ways. Also, it is to be understood that the phraseology and terminology employed herein is for the purpose of description and should not be regarded as limiting.

Method of Moving Small Objects

A first aspect of the present invention is of a method for moving a small object from a first location to a second location, where preferably the relative position of the locations to each other is fixed.

By small object is meant an object having dimensions in the order of less than $10^3$ microns, or even less than $10^2$ microns, or even less than $10^1$ microns or even less than $10^0$ microns. Such objects include cells but also small particles, crystals, bacteria, viruses, proteins, polymers, macromolecules and ions.

Figure 1B:
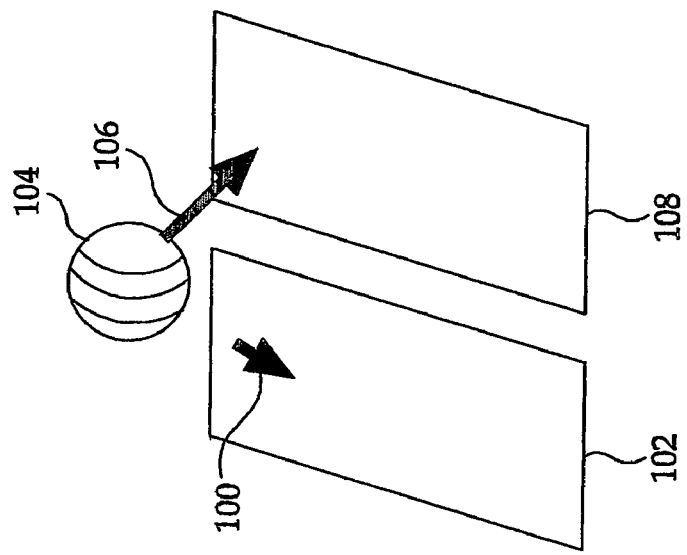

The simplest embodiment of the method of the present invention, depicted in FIG. 1, involves:

a. applying a first attractive force 100 from a first location 102 on a small object 104, in order to localize small object 104 at first location 102 (FIG. 1A); and b. thereafter applying a second attractive force 106 from a second location 108 on small object 104 (FIG. 1B).

As is clear to one skilled in the art, in such a way small object 104 is transferred from first location 102 to second location 108. As is also clear to one skilled in the art, the proximity and relative spatial orientation of first location 102 and second location 108 must be selected so as to allow efficient transfer of small object 104.

To expedite the transfer of small object 104, the intensity of first attractive force 100 is preferably reduced or eliminated. Reduction or elimination of first attractive force 100 occurs before, during or after application of second attractive force 106. In some embodiments of the method of the present invention the first attractive force is not only reduced but also reversed to be a repulsive force. In such a case, the small object is sequentially or simultaneously repelled from first location 102 and attracted to second location 108, FIG. 2.

Figure 2C:
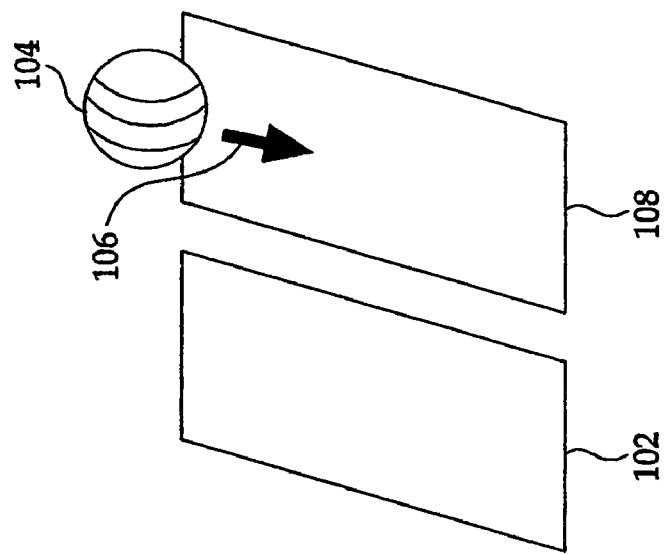
FIGS. 2A-2C illustrate the method of the present invention for moving a small object from one location to a neighboring location using attractive and repulsive forces.
Figure 2B:
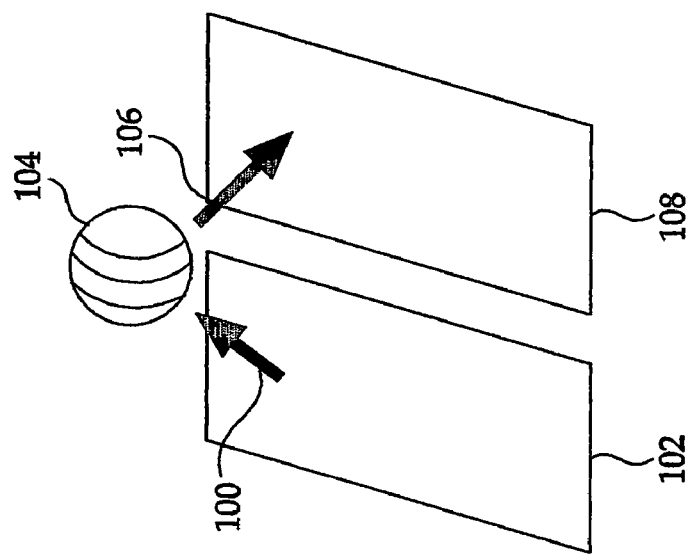
Figure 2A:
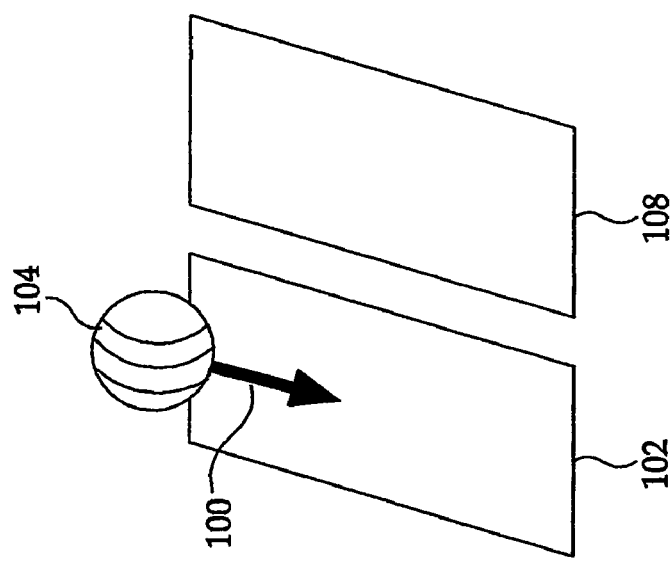
Figure 3:
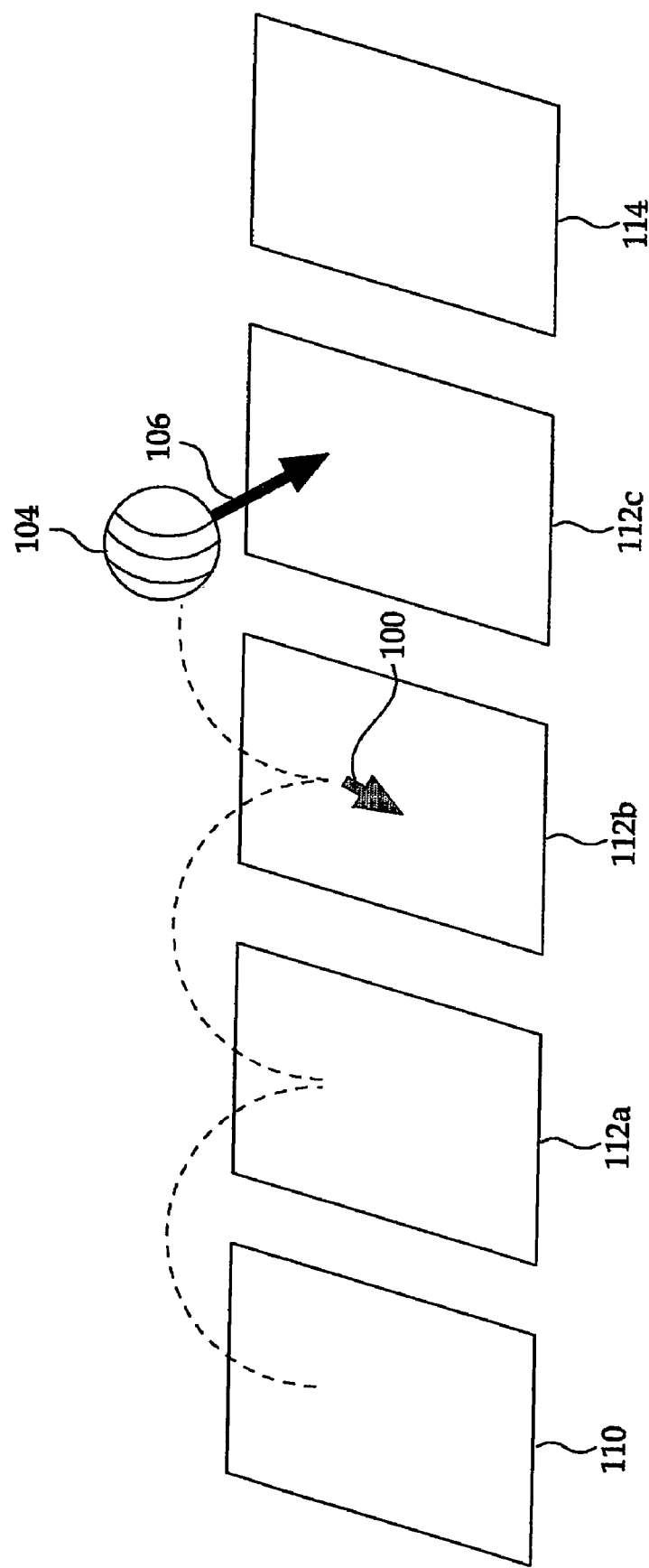
FIG. 3 illustrates the method of the present invention for moving a small object from one location to a non-neighboring location by a series of successive transfers to a series of neighboring locations.

The method of the present invention is preferably applied to the moving of some small object from some initial location to some destination location by the movement of the small object through a succession of intermediate locations until the small object arrives at the destination location. Preferably, the position of the locations relative to each other is fixed. This process is schematically depicted in FIG. 3 for the movement of small object 104 from an initial location 110 to a destination location 114 by the movement of small object 104 from initial location 110 through a succession of three intermediate locations 112a, 112b and 112c until small object 104 arrives at destination location 114. The movement of small object 104 between any two locations is analogous to the movement between first location 102 and second location 108 as depicted in FIG. 1 and FIG. 2 discussed hereinabove.

When the method of the present invention is applied to a system where there are more than two locations then any two locations are related to each other in one of two ways: neighboring and not-neighboring. Neighboring locations are those locations where to a small object can be directly transferred in one step. Non-neighboring locations are those locations where to a small object can be transferred only via other locations. In FIG. 3, location 110 and location 112b are neighboring to location 112a. However location 110 is not-neighboring to location 112b.

The physical nature of the different locations as well as the nature of the respective attractive and, if implemented, repulsive forces depends on the size and nature of the small objects to be manipulated.

The attractive and repulsive forces can be physical, electrical, magnetic or any combination thereof. Electric forces can include those made by charging a surface, but can also be of chemical origin such as ionic bonds or hydrogen bonds. Preferably the attractive and repulsive forces are implemented by a flow of a physical medium such as a gas or a liquid. When an attractive force is generated by the flow of a physical medium, then the attractive force associated with a location is generally implemented by suction of a fluid through or in the immediate vicinity of that location. When a repulsive force is generated by the flow of a physical medium, then the repulsive force associated with a location is generally implemented by injection of a fluid through or in the immediate vicinity of that location.

As stated above, the physical nature of the locations is determined by the size and nature of the small object to be manipulated and the nature of the forces applied to manipulate the object. In some embodiments of the present invention, the locations are simply areas, for example, on a surface, defined by the proximity of a respective attractive force. In other embodiments, the designated locations are dimples or recesses on a surface.

In preferred embodiments of the present invention, especially suited for the manipulation of cells, the locations are trapping enclosures (e.g., chambers or tubes) configured to substantially physically contain (partially or completely) a small object, such as a cell. In such preferred embodiments, schematically depicted in FIG. 4 in cross section, a trapping enclosure 116 is provided with an open trapping-end 118 through which a respective attractive or repulsive force is applied and through which a manipulated small object 120 enters and exits trapping enclosure 116. It is preferred that the dimensions of open trapping-end 118 are such that only one small object 120 can enter trapping enclosure 116 at one time and that once a first small object 120 enters any other small object, e.g. 122, is blocked from entering trapping enclosure 116. The geometry of open trapping-end 118 is not generally of significance and can be fashioned in any shape, for example, square, circular or hexagonal.

Figure 4:
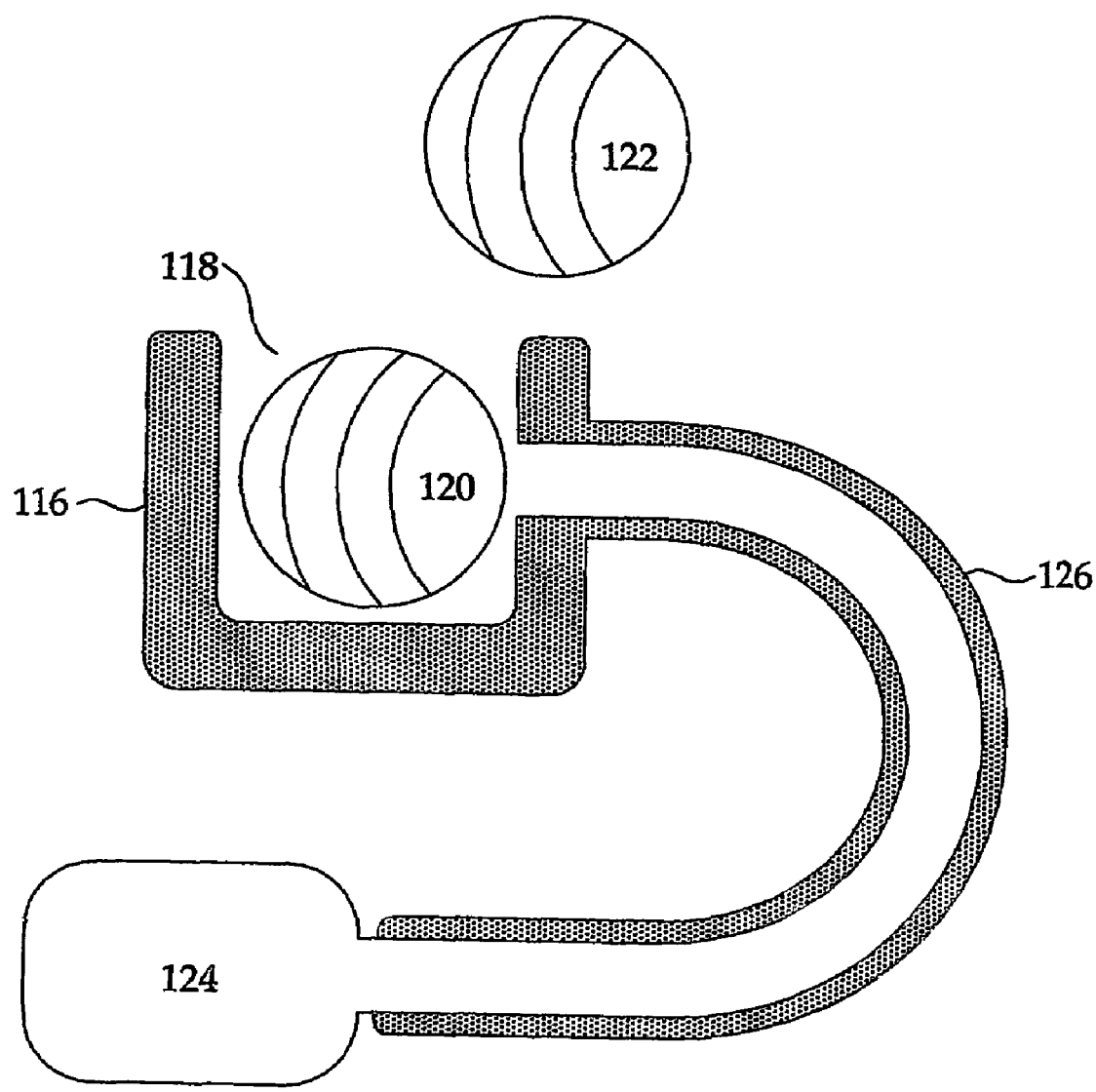
FIG. 4 is a schematic depiction of a location of the present invention implemented with a trapping enclosure.

Cells are ordinarily found in a liquid medium. Thus, for embodiments of the present invention directed to the manipulation of cells, an attractive force is preferably implemented using a flow generator 124 operated in a suction mode. Analogously, in such embodiments a repulsive force is preferably implemented using a flow generator 124 operated in an injection mode. The inlet/outlet of flow generator 124 is preferably attached to trapping enclosure 116 in a way so that attractive and repulsive forces act through open trapping-end 118. In FIG. 4, the inlet/outlet of flow generator 124 is attached to trapping enclosure 116 through conduit 126 which emerges inside trapping enclosure 116.

By a flow generator is meant a device or other means to generate a flow with a desired direction in a fluid. An example of a flow generator is a pump or plurality of pumps. In some embodiments a flow generator include valves and the like.

For embodiments of the present invention directed to the manipulation of cells, the fluid preferably used is a liquid media, especially a cell culture media. Many different cell culture media are known to one skilled in the art. Examples of cell culture media that are useful in implementing the teachings of the present invention include but are not limited to Dulbecco's minimal essential medium, Hank's medium and those listed in U.S. Pat. No. 6,692,961, U.S. Pat. No. 6,689, 594, U.S. Pat. No. 6,686,190, U.S. Pat. No. 6,673,591, U.S. Pat. No. 6,670,184, U.S. Pat. No. 6,670,180, U.S. Pat. No. 6,667,034, U.S. Pat. No. 6,660,501, U.S. Pat. No. 6,649,408, U.S. Pat. No. 6,642,050, U.S. Pat. No. 6,635,448, U.S. Pat. No. 6,627,426, U.S. Pat. No. 6,610,516, U.S. Pat. No. 6,593,140, U.S. Pat. No. 6,589,765, U.S. Pat. No. 6,588,586, U.S. Pat. No. 6,569,422, U.S. Pat. No. 6,555,365, U.S. Pat. No. 6,544,788, U.S. Pat. No. 6,528,286, U.S. Pat. No. 6,511,430, U.S. Pat. No. 6,506,598, U.S. Pat. No. 6,492,163, U.S. Pat. No. 6,492,148, U.S. Pat. No. 6,489,144, U.S. Pat. No. 6,479,252, U.S. Pat. No. 6,468,788, U.S. Pat. No. 6,465,205, U.S. Pat. No. 6,465,000, U.S. Pat. No. 6,455,310, U.S. Pat. No. 6,413,746, U.S. Pat. No. 6,413,744, U.S. Pat. No. 6,410,309, U.S. Pat. No. 6,403,369, U.S. Pat. No. 6,383,810, U.S. Pat. No. 6,378,527, U.S. Pat. No. 6,372,494, U.S. Pat. No. 6,344,354, U.S. Pat. No. 6,342,384, U.S. Pat. No. 6,338,964, U.S. Pat. No. 6,333,192 and U.S. Pat. No. 6,329,195.

When manipulating a small object according to the present invention it is often advantageous to hold the small object at a given location for a desired length of time. Holding a small object at a given location can be implemented in many different ways. One preferred method of holding a small object at a given location is by the continuous application of an associated attractive force. In FIG. 4, such a method is implemented by continuously activating flow generator 124 in suction mode. The use of such a method of holding the small object in place is generally contingent on the presence of a "stop", that is a physical impediment to small object 120 being sucked into flow generator 124 by the attractive force. In FIG. 4 the stop is substantially the small dimension, relative to the size of small object 120, of conduit 126.

Another preferred method of holding a small object at a given location is by relying on the nature of the small object and the geometry of the location to prevent drifting of the small object away from the location. In FIG. 4, such a method is implemented by setting flow generator 124 to inactive mode, a mode where neither an attractive nor a repulsive force is applied. Due to the small size of open trapping-end 118 and the lack of currents inside trapping enclosure 116, small object 120 remains trapped in the location defined by trapping enclosure 116.

In one embodiment of the present invention, locations are disposed in a one-dimensional array, understood to mean that any location has at most two neighboring locations. Examples of one-dimensional arrays include linear arrangements of locations, curved arrangements of locations and circular arrangements of locations.

Figure 5:
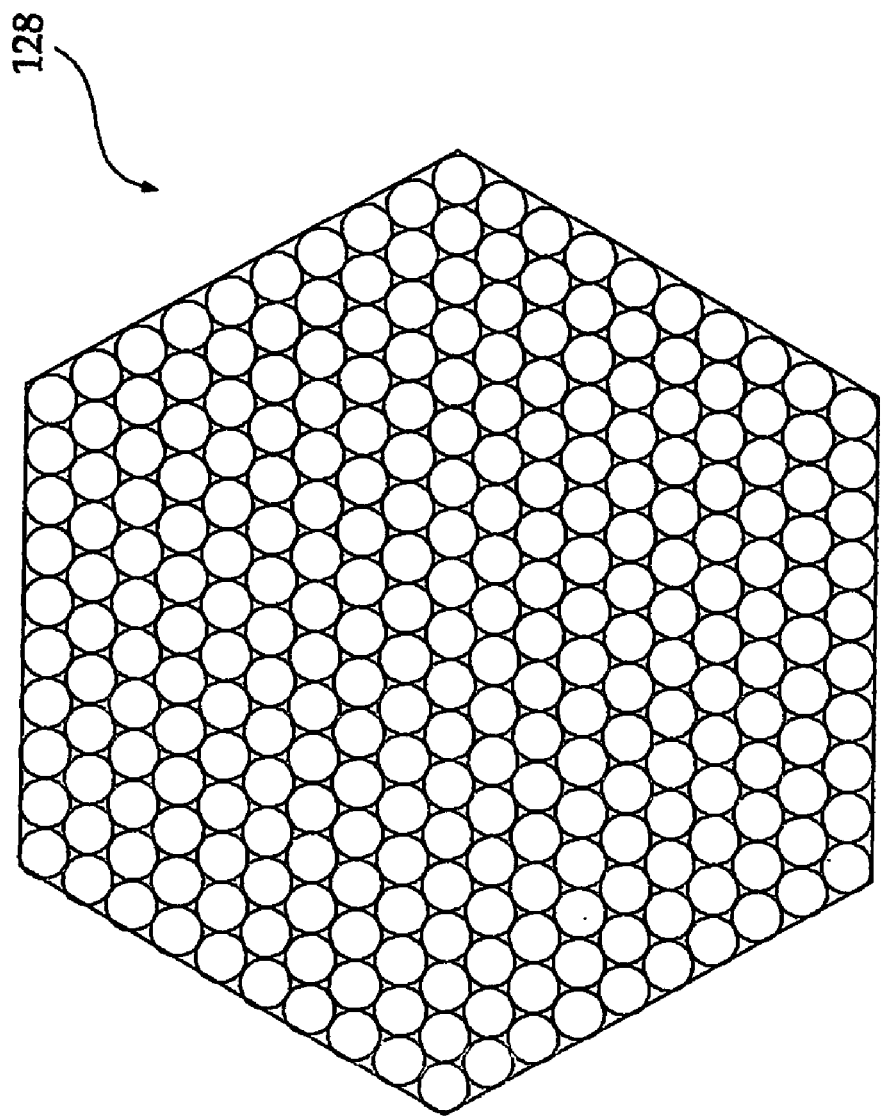
FIG. 5 is a schematic depiction of a hexagonal matrix of locations of the present invention.

In another embodiment of the present invention, locations are disposed in a two-dimensional array, understood to mean that at least one given location has more than two neighboring locations. Two-dimensional arrays include Y-shaped and X-shaped arrays. Preferably a two-dimensional array of the present invention is a matrix arrangement, that is a regular arrangement of a multiplicity of locations. One preferred matrix arrangement of locations is a square lattice, where substantially each non-edge location has four neighboring locations. Another preferred matrix arrangement of locations is a hexagonal lattice, where substantially each non-edge location has six neighboring locations. In FIG. 5 a hexagonal matrix of locations 128 is depicted, each location 128 having a circular cross section.

It is important to note that for the sake of simplicity, arrays of locations are depicted and described herein as being substantially planar, that is, the locations or the open trapping-ends of the locations as a group substantially define a plane. This is done exclusively for the sake of simplicity of explanation. In some embodiments of the present invention a matrix of locations implementing the method of the present invention may be non-planar.

Cell Manipulation Device

For the manipulation of cells the method of the present invention is preferably implemented using a cell-manipulation device of the present invention, the cell-manipulation device including at least two (but preferably a multiplicity) of cell-manipulation elements of the present invention, the at least two (or the multiplicity) of cell-manipulation elements defining a cell-manipulation probe of the present invention.

A preferred embodiment and the currently known best mode of implementing the device of the present invention is described hereinbelow and with reference, inter alia, to FIG. 6. It is understood that cell-manipulation device 130 depicted in FIG. 6 and described hereinbelow is a particular specific device suitable for manipulating cells in a liquid medium, and described herein exclusively for exemplary purposes.

Figure 6A:
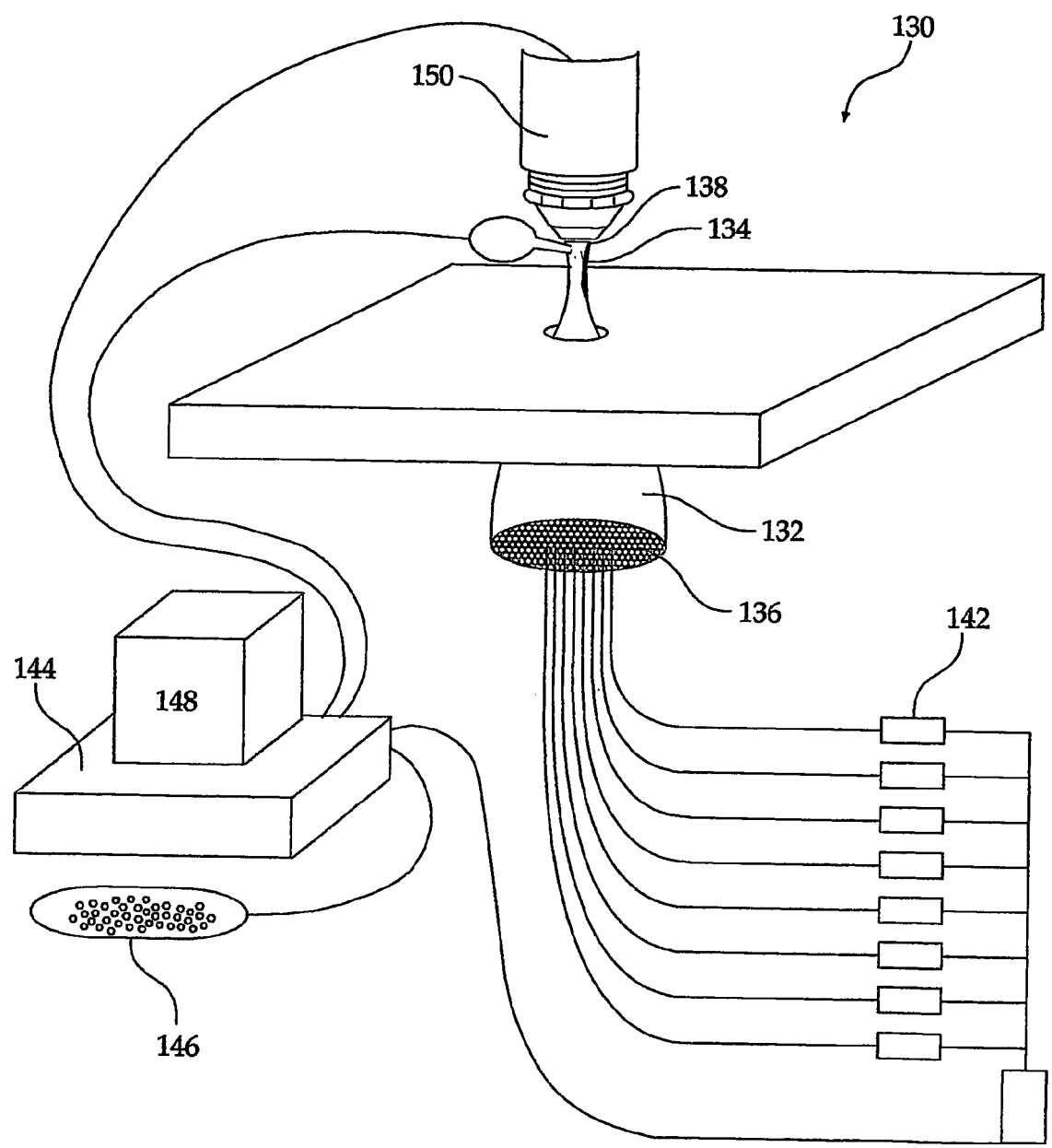
FIG. 6A is a schematic depiction of a preferred embodiment of the cell manipulation device of the present invention.

The central component of device 130, a cell-manipulation probe 132 having a probe-end 134 and a butt end 136 is depicted in FIG. 6A. Surrounding probe-end 134 is vial 138. Cell manipulation probe 132 is made up of a multiplicity of bundled cell-manipulation elements. Functionally associated with each cell-manipulation element is one, two, three or even more independently controllable pumps 142. Each pump 142 is connected to a respective cell-manipulation element through butt end 136 of cell manipulation probe 132. For clarity, only a limited number of pumps 142 and connections to cell-manipulation elements are depicted in FIG. 6A. Controlling the activation of pumps 142 is central control unit 144, substantially a programmable computer with necessary hardware and software to receive commands from a user input interface 146, to perform the received commands, for example by performing necessary calculations or activating a specific pump 142, and to display information using a user output interface 148. Device 130 is also provided with an observation component 150, such as but not limited to a CCD camera equipped with a microscope lens. Observation component 150 in FIG. 6A is functionally associated with central control unit 144. Observation component 150 receives commands from central control unit 144 and returns data corresponding to acquired images, especially of cells manipulated at probe-end 134 of cell manipulation probe 132. Central control unit 144 is configured to display data received from observation component 150 and display the data in user understandable form through user output interface 148. It is preferred that central control unit 144 be configured with image processing capabilities so as to "interpret" video data received from observation component 150 and react to the interpreted data.

Figure 6B:
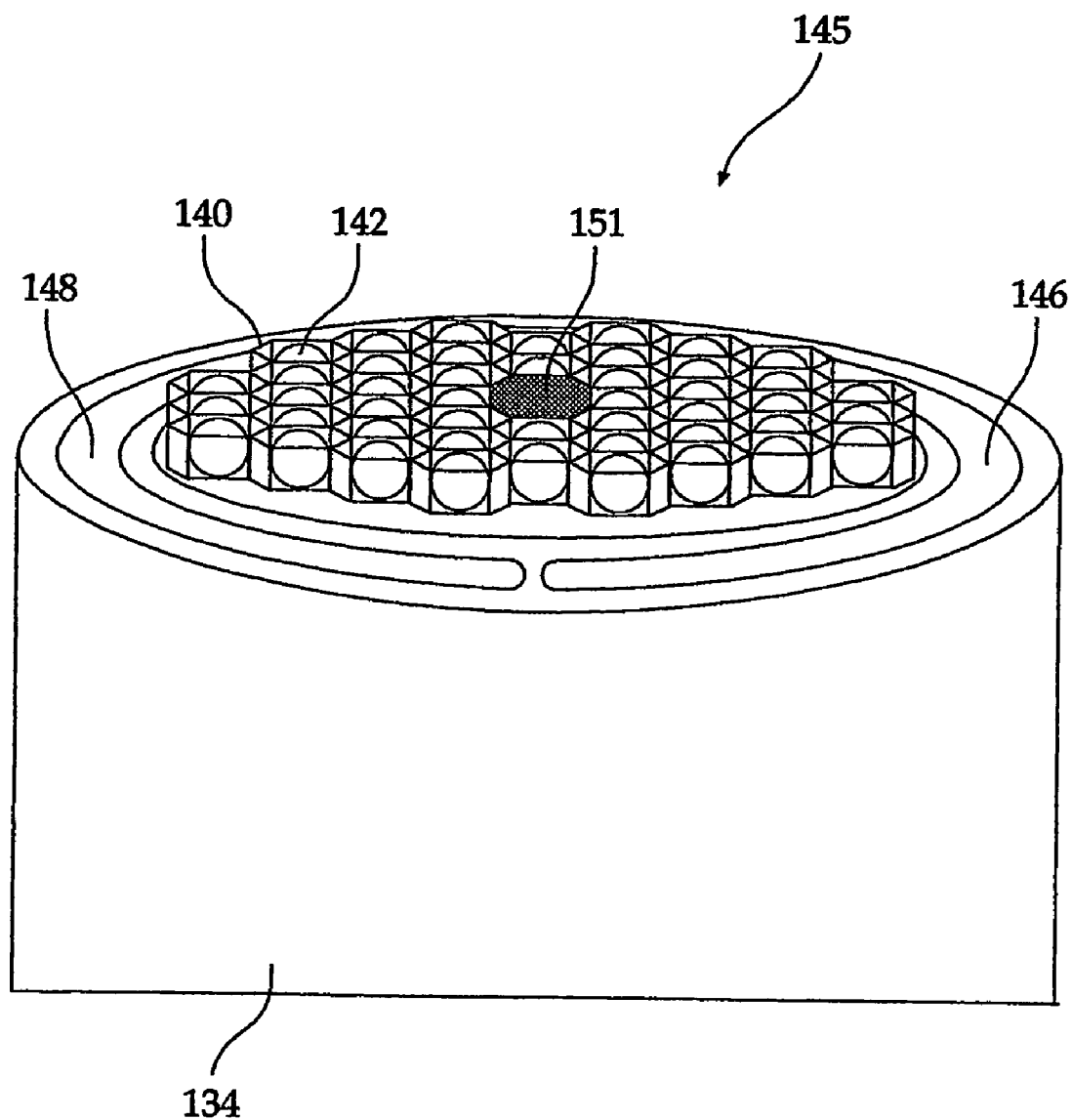
FIGS. 6B and 6C are schematic depictions of the tip of a preferred embodiment of a probe tip end of a cell manipulation probe of the present invention.

In FIG. 6B, a close-up of probe-end 134 of cell-manipulation probe 132 without vial 138 is depicted. A multiplicity of hexagonal trapping enclosures 140, each being a part of a cell-manipulation element, are depicted with a cell 142 trapped therein. Trapping enclosures 140 are arrayed in a matrix 145. A semi-circular isolation inlet 146 of an isolation element and a semi-circular waste inlet 148 of a waste element are positioned at the circumference of matrix 145. In the center of matrix 145 is a multi-cell reaction enclosure 151 of a multi-cell reaction element.

Figure 6C:
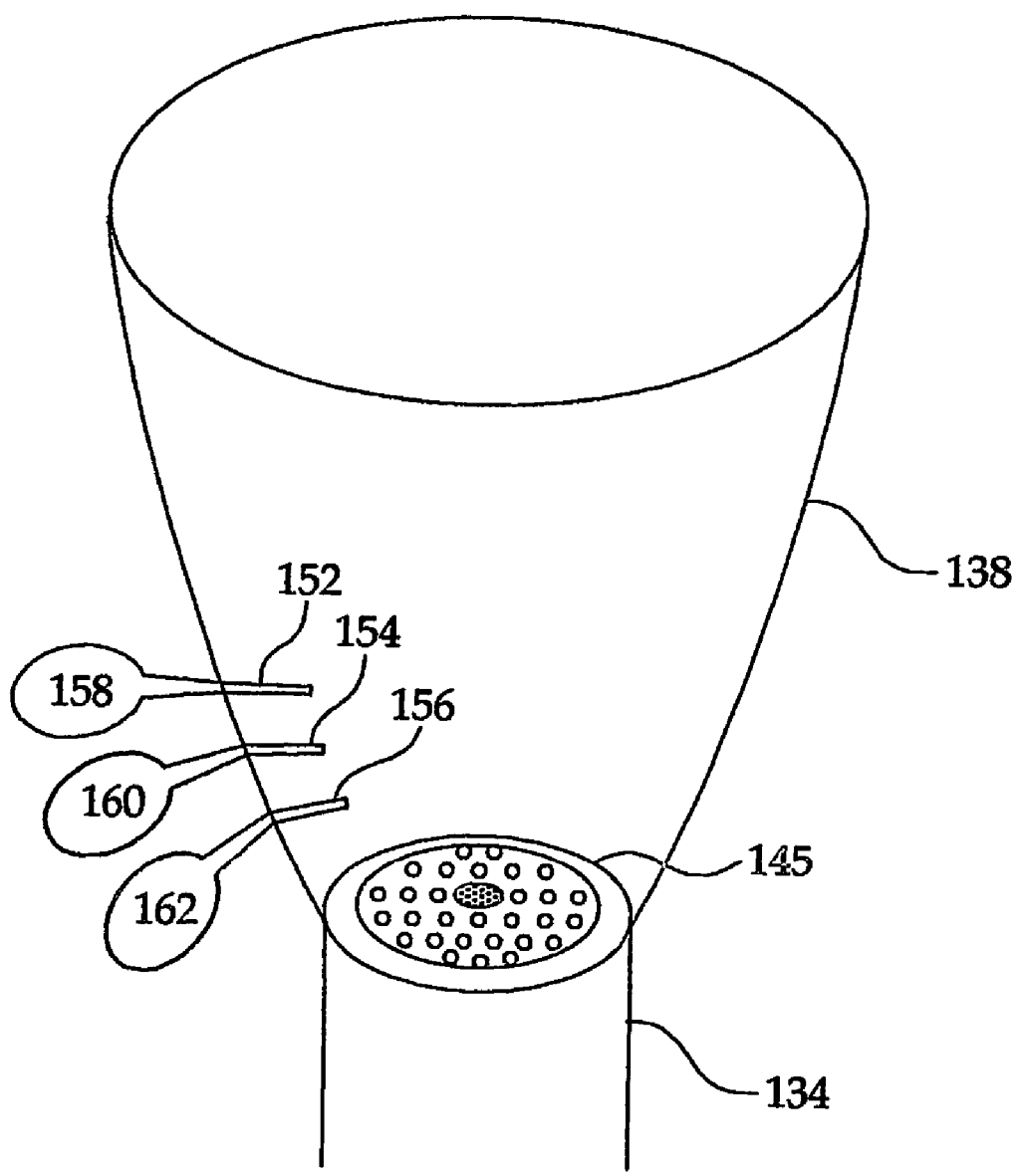

In FIG. 6C, probe-end 134 of cell manipulation probe 132 with vial 138 is depicted close-up. Emerging into vial 138 are sample inlet 152, fluid inlet 154 and vial reagent inlet 156. Each such inlet is functionally associated with a respective pump 158, 160 and 162 to allow introduction of samples, fluid or reagents, respectively, onto probe-end 134. Pumps 158, 160 and 162 are independently controllable by central control unit 144.

Cell-Manipulation Elements

As stated hereinabove, cell-manipulation probe 132 is substantially made up of a multiplicity of individual cell-manipulation elements. There are many variations of cell-manipulation elements, some of which are discussed hereinbelow.

Types of Cell-Manipulation Elements

One simple cell manipulation element preferred in implementing a device of the present invention is a dimple on a surface, where at the bottom of the dimple is the inlet of an functionally associated flow generator having two modes: a suction mode (to generate an attractive force) and an inactive mode. When the flow generator is set to suction mode, a cell is attracted and held at the associated dimple by the produced suction. When the pump is set to inactive mode, the held cell may drift away. If a pump functionally associated with a neighboring dimple is set to suction mode, the cell drifts towards and is held in that neighboring dimple in accordance with the method of the present invention. Although such a cell manipulation element is simple to produce and operate, and a cell-manipulation probe made of an array of such cell manipulation elements effectively implements the method of the present invention, the utility of such a cell-manipulation probe is limited as it is difficult to expose only selected cells to stimuli such as reagents, vide infra.

For embodiments of the present invention directed to the manipulation of cells, it is generally preferred that a cell manipulation element have a trapping enclosure with an open trapping end as depicted in FIG. 4. The trapping enclosure is configured so as to substantially physically contain (partially or completely) a cell held therein while the open trapping end provides access of cells into and out of the trapping enclosure. In such a way a cell in the trapping enclosure is isolated, allowing selective exposure of cells to stimuli such as reagents. The inlet/outlet of a flow generator associated with a cell manipulation element having a trapping enclosure advantageously emerges within the trapping enclosure. In some embodiments such a flow generator has only two modes: a suction mode and an inactive mode. In a preferred embodiment, such a trapping enclosure is configured or shaped so that when the flow generator applies no force (e.g. is set to inactive mode), a held cell is retained within the trapping enclosure. When the trapping enclosure is so configures, an associated flow generator preferably has at least three modes: a suction mode (to generate an attractive force), an injection mode (to generate a repulsive force) and an inactive mode. When the flow generator is set to suction mode, fluid is drawn from a trapping enclosure through a respective conduit generating an attractive force to pull a nearby cell into the trapping enclosure. When the flow generator is set to inactive mode, a held cell remains within the trapping enclosure. When the flow generator is set to injection mode, fluid is injected into a trapping enclosure through a respective conduit generating a repulsive force to eject a held cell from the trapping enclosure.

It is generally preferred that a trapping enclosure and an open trapping end of a cell manipulation element have dimensions close to those of the cell to be held and manipulated. As is known to one skilled in the art, cells of various sizes exist. Plant cells are typically large, having a diameter of between $10^1$ to $10^2$ microns. Animal cells typically have a diameter of between $10^{-1}$ to $10^2$ microns. Bacteria are typically small, having a diameter of between $10^{-1}$ to $10^{-2}$ microns. It is therefore preferred that the dimensions of the open trapping ends of the trapping enclosure be determined by the size of cells that are to be studied with a specific device of the present invention.

Cell Manipulation Elements Associated with a Single Conduit Pump

Figure 7A:
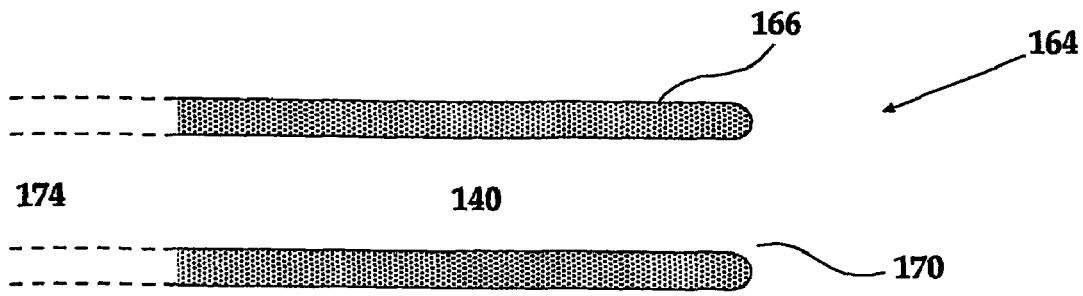
FIG. 7A is a cross section view of a schematic depiction of a preferred embodiment of a cell manipulation element with a single conduit.

A simple cell manipulation element 164 implementing a trapping enclosure is schematically depicted in FIG. 7A. Cell manipulation element 164 is substantially a tube 166 functionally associated with a conduit pump (not depicted), the conduit pump operable in a suction mode, an injection mode and an inactive mode. In cell-manipulation element 164 the end of tube 166 serves as an open trapping-end 170 and the bore of tube 166 serves as a trapping enclosure 140. The bore of tube 166 also serves as a conduit 174 for transporting fluid from the functionally associated conduit pump to attract and repel a cell in accordance with the teachings of the present invention.

It is often preferred that a cell manipulation element have a cell stop, a physical obstruction limiting the extent of penetration of a cell inside a cell manipulation element. Depending on the specific embodiment, a cell stop is a narrowing, a protrusion or other physical structural feature that limits the distance into an functionally associated trapping enclosure that a cell can be drawn.

Figure 7B:
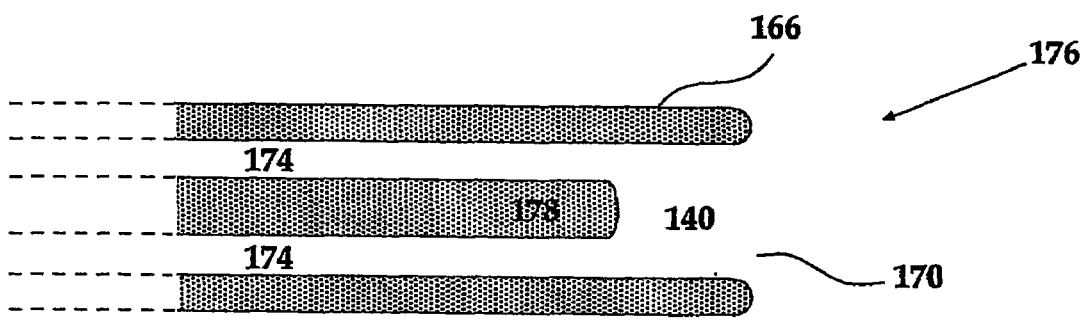
FIG. 7B is a cross section view of a schematic depiction of a preferred embodiment of a cell manipulation element with a single conduit and a cell stop.

A preferred cell manipulation element 176 integrating a cell stop is depicted in FIG. 7B. Cell manipulation element 176 is similar to cell manipulation element 164 except that cell manipulation element 176 is also provided with a cell stop 178. Cell stop 178 obstructs the bore of tube 166 so that a cell entering through open trapping-end 170 penetrates until making contact with cell stop 178. Trapping enclosure 140 of cell manipulation element 176 is defined by the inside surface of tube 166 and cell stop 178. The volume between cell stop 178 and tube 166 serves as a single conduit 174 for transporting fluid from a functionally associated conduit pump to attract and repel a cell in accordance with the teachings of the present invention. It is important to note that in some embodiments conduit 174 has an annular cross section. In other embodiments conduit 174 is made of a multiplicity of individual fluid paths peripherally arrayed about cell stop 178. In such an embodiment, all the individual fluid paths preferably transport fluid from a single conduit pump.

Figure 7C:
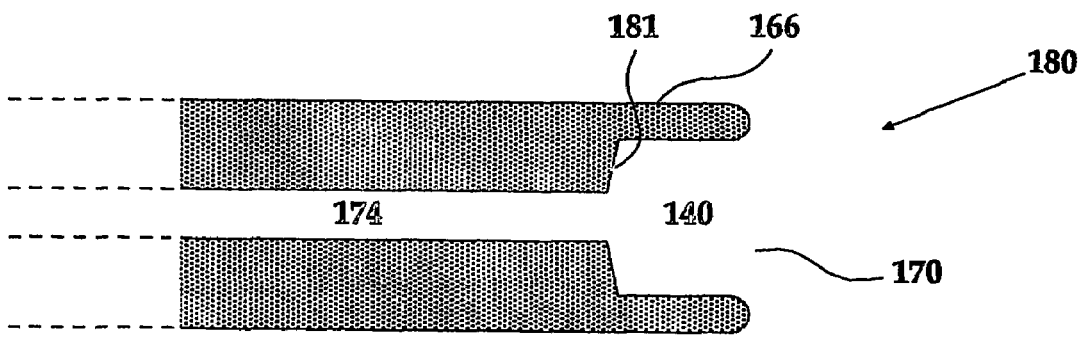
FIG. 7C is a cross section view of a schematic depiction of a preferred embodiment of a cell manipulation element with a single conduit and a bore narrowing.

An additional cell manipulation element 180 integrating a cell stop is depicted in FIG. 7C. In cell manipulation element 180 the function of a cell stop is performed by a narrowing 181 of the bore of tube 166 to an extent that a cell entering through open trapping-end 170 cannot penetrate beyond narrowing 181. Thus, trapping enclosure 140 of cell manipulation element 180 is defined by the inside surface of tube 166 and narrowing 181 in the bore of tube 166. As in cell manipulation element 164, the bore of tube 166 serves as a conduit 174 for fluid from a functionally associated conduit pump.

Cell manipulation elements 164, 176 and 180 are all operated in a substantially similar way. Central control unit 144 sets a functionally associated conduit pump to suction mode, producing an attractive force through conduit 174 to attract cells in the vicinity of an open trapping-end 170 to enter cell manipulation element 164, 176 or 180 through an open trapping-end 170 and to be trapped in a trapping enclosure 140. When cell manipulation element 164 is used, central control unit 144 sets a functionally associated conduit pump to inactive mode when a cell enters open trapping-end 170 to prevent penetration of the cell too far into the bore of tube 166 and consequent loss of the cell. It is thus generally preferred to use a cell manipulation element such as 164 under observation of an observation component 150. In contrast, a cell entering open trapping-end 170 of a cell manipulation element 176 or 180 makes contact with a functionally associated cell stop 178 or narrowing 181, respectively, and thus remains held in trapping enclosure 140.

When it is desired to eject a cell from a trapping enclosure 140 of a cell manipulation element 164, 176 or 180, central control unit 144 sets a respective functionally associated conduit pump to injection mode. Fluid is forced through conduit 174 pushing a held cell outwards from trapping enclosure 140 through open trapping end 170.

Cell Manipulation Elements Functionally Associated with Multiple Conduit Pumps

To increase the flexibility of the types of cell manipulations that can be performed using a device of the present invention, it is often advantageous to use a cell manipulation element having more than one conduit and functionally associated with more than one independently controllable conduit pump.

Figure 7D:
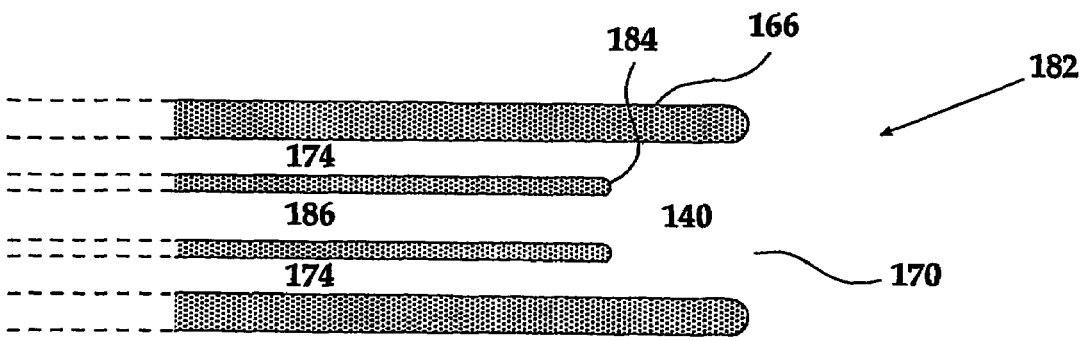
FIG. 7D is a cross section view of a schematic depiction of a preferred embodiment of a cell manipulation element with an axial conduit and one peripheral conduit.

Cell manipulation element 182, depicted in FIG. 7D, has more than one conduit and is functionally associated with more than one independently controllable conduit pump. Cell manipulation element 182 is related to cell manipulation element 176 in that a trapping enclosure 140 is defined by the inside surface of a tube 166 and by a cell stop 184. Further, the volume between tube 166 and cell stop 184 serves as a first peripheral conduit 174 for fluid from a functionally associated first conduit pump. Cell manipulation element 182 is characterized, however, in that cell stop 184 is substantially a hollow tube. The bore of cell stop 184 serves as a second axial fluid conduit 186 transporting fluid from an independently controlled and activated second conduit pump.

Figure 7E:
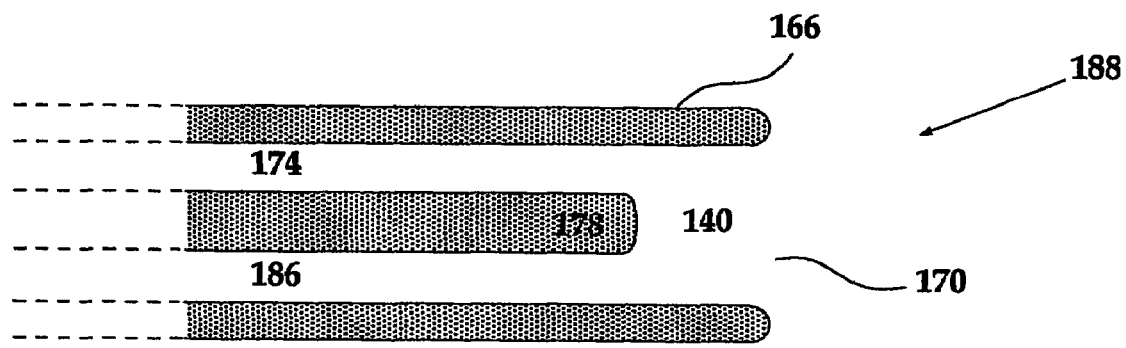
FIG. 7E is a cross section view of a schematic depiction of a preferred embodiment of a cell manipulation element with two peripheral conduits.

An additional preferred cell manipulation element functionally associated with more than one independently controllable conduit pump is 188 depicted in FIG. 7E. Cell manipulation element 188 is related to cell manipulation element 176 in that a trapping enclosure 140 is defined by the inside surface of a tube 166 and by a cell stop 178. However, in cell manipulation element 178, the volume between tube 166 and cell stop 178 does not have an annular cross section but is rather made up of at least two distinct conduits found at the periphery of tube 106, a first peripheral conduit 174 and a second peripheral conduit 186. First peripheral conduit 174 is functionally associated with a first conduit pump. Second peripheral conduit 186 is functionally associated with an independently controlable second conduit pump.

It is important to note that variants of cell manipulation element 188 are provided with more than two (e.g. three, four, five, six or even more) conduits (especially peripheral conduits) each such conduit associated with an individually controllable conduit pump.

For loading a cell into a cell manipulation element functionally associated with two independently controllable pumps, a functionally associated first conduit pump and/or second conduit pump are set to suction mode by central control unit 144. If only one associated conduit pump is used, the other associated conduit pump is set to inactive mode. Analogously, ejection of a cell from trapping enclosure 140 of cell manipulation element 182 is performed when a functionally associated first conduit pump and/or second conduit pump are set to injection mode by central control unit 144. If only one associated conduit pump is used, the other associated conduit pump is set to inactive mode.

A useful function that can be implemented using a cell manipulation element functionally associated with two or more independently controllable conduit pumps is washing of a cell held in a respective trapping enclosure 140. For a cell manipulation element 188, central control unit 144 sets one functionally associated conduit pump to suction mode and the other functionally associated conduit pump to injection mode. Liquid flows from one conduit to another, thus washing a cell held in trapping enclosure 140. For a cell manipulation element 182, central control unit 144 sets a first conduit pump functionally associated with peripheral conduit 174 to injection mode and sets a second conduit pump functionally associated with axial conduit 186 to suction mode. Liquid flows from one conduit to the other, thus washing a cell held in trapping enclosure 140.

A useful function that can be performed using cell manipulation element 182 is suspending a cell held in trapping enclosure 140 at a distance from open trapping-end 170. To perform the suspension function, central control unit 144 sets the conduit pump functionally associated with axial conduit 186 to injection mode while setting the conduit pump functionally associated with peripheral conduit 174 to suction mode. The resulting Venturi effect suspends a cell originally trapped in trapping enclosure 140 above open trapping-end 170. The suspension function allows a cell to be temporarily removed from trapping enclosure 140 to allow clear, unimpeded examination of the cell from many directions, a challenging task when a cell is contained within trapping enclosure 140. The suspension function as described hereinabove may be generally performed with a properly configured cell manipulation element having at least one axial conduit and at least one peripheral conduit. If there is only one peripheral conduit, that peripheral conduit is preferably substantially annular. If there is more than one peripheral conduit, the peripheral conduits are preferably arrayed symmetrically about the axial conduit.

An additional useful function that can be implemented using a cell manipulation element functionally associated with two or more independently controllable conduit pumps, such as 182 or 188, is selective exposure of a cell held in trapping enclosure 140 to a reagent. The function of selectively exposing a cell to a reagent will be discussed herein with reference to a cell manipulation element 188. In one embodiment, exposure is performed by providing one of the two conduit pumps functionally associated with cell manipulation element 188 with a reagent. When it is desired to selectively expose a cell to the reagent, a process analogous to washing a cell as described above is followed. The associated conduit pump provided with reagent is set to injection mode bringing reagent into trapping enclosure 140 and thus to contact a cell held therein. In parallel the second associated conduit pump is set to suction mode, drawing away reagent and preventing leakage of reagent out through a open trapping-end 170. A disadvantage of such an implementation is that a conduit pump provided with reagent cannot be used for performing other functions.

Selective exposure of a cell can also be achieved in a cell manipulation element provided with three conduits each functionally associated with an independently controllable conduit pump, where one conduit is dedicated to providing reagent and the other two conduits only for performing other functions.

Figure 7F:
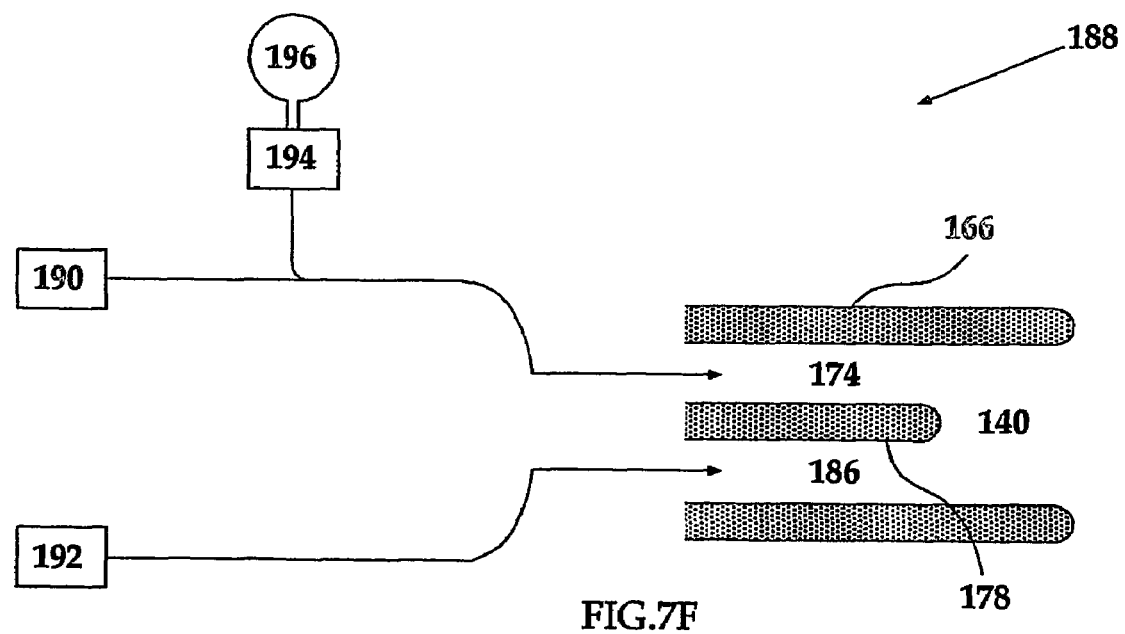
FIG. 7F is a diagram depicting a pump system useful for introducing reagents through a cell manipulation element.

In a preferred embodiment for implementing selective exposure of cells to a reagent, a cell manipulation element is functionally associated with three pumps as depicted in FIG. 7F. In FIG. 7F is depicted a cell manipulation element 188 where conduit 174 is functionally associated with a first conduit pump 190 and conduit 186 is functionally associated with a second conduit pump 192. On the fluid-line connecting conduit 174 with first conduit pump 190 is reagent injection pump 194. Similarly, to the cell washing function discussed hereinabove, when it is desired to expose a cell to a reagent, central control unit 144 sets first conduit pump 190 to injection mode and second conduit pump 192 to suction mode. Further, central control unit 144 sets reagent injection pump 194 to injection mode, causing reagent from a container 196 to enter the flow of first conduit pump 190 towards conduit 174. The reagent is transported through conduit 174, exposing a cell held in trapping enclosure 140 to the reagent. Reagent is then pumped away through conduit 186 by the action of second conduit pump 192, drawing away reagent and preventing leakage of reagent out through a open trapping-end 170.

Cell Manipulation Elements Having a Tool for Penetrating a Cell Wall

It is often advantageous to be able to introduce one or more reagents directly into a cell or to extract a sample from inside a cell. To this end, in a preferred embodiment of the present invention, a cell manipulation element is provided with a tool configured to penetrate a cell wall. Such a tool is, for example, a pointed solid object, for example from glass or metal. Preferably, such a tool is disposed inside the trapping enclosure of the cell manipulation element in such a way that when an attractive force according to the present invention is applied, the cell is pulled against the tool and the cell wall consequently penetrated.

Figure 7G:
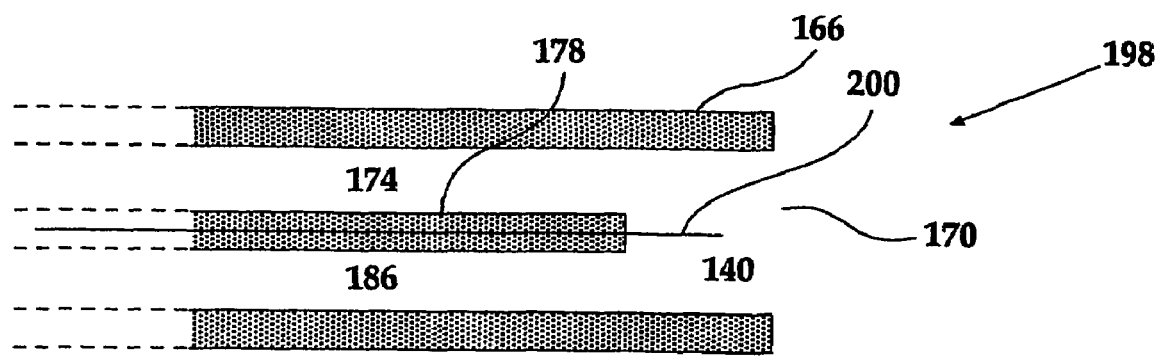
FIG. 7G is a cross section view of a schematic depiction of a preferred embodiment of a cell manipulation element with a cell wall penetrating tool.

In FIG. 7G a cell manipulation element 198 analogous to cell manipulation element 188 is depicted, having a cell wall penetrating tool 200. Cell wall penetrating tool 200 is a stainless steel wire inside cell stop 178. To penetrate the wall of a cell, the cell is brought into trapping enclosure 140. Conduit pumps functionally associated with conduits 174 and 186 are set to suction mode. The resulting attractive force pulls the cell onto cell wall penetrating tool 200, thus penetrating the cell wall. Post-penetrating cell release is accomplished by setting the functionally associated conduit pumps to injection mode so that the resulting liquid flow through conduits 174 and 186 pushes the penetrated cell off of cell wall penetrating tool 200.

Advantageous is that once a cell wall is penetrated, a reagent is injected into the penetrated cell or the contents of the penetrated cell are sampled. In a preferred embodiment that a cell wall penetrating tool has a conduit functionally associated with an independently controllable pump for injecting reagents or sampling cell contents through the conduit.

Figure 7H:
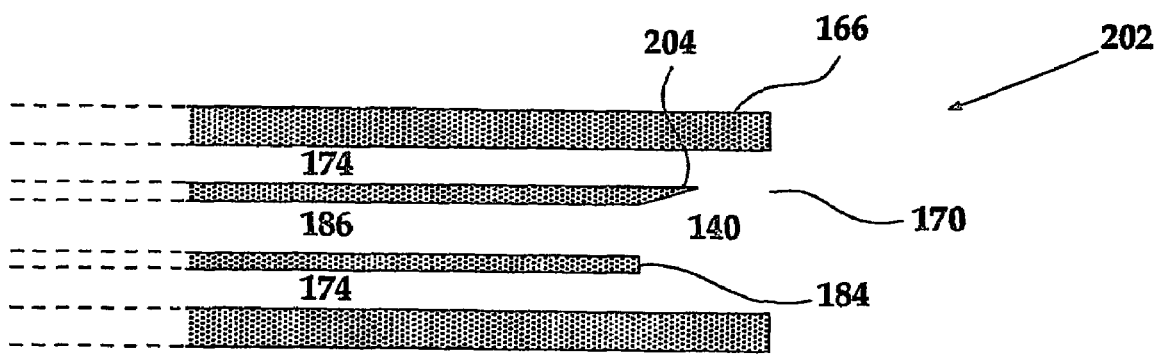
FIG. 7H is a cross section view of a schematic depiction of a preferred embodiment of a cell manipulation element with an axial conduit equipped with a cell wall penetrating tool.

In FIG. 7H a cell manipulation element 202 analogous to cell manipulation element 182 is depicted, having a cell wall penetrating tool 204. Cell wall penetrating tool 204 is substantially a sharpened tip of hollow cell stop 184. To penetrate the wall of a cell, the cell is brought into trapping enclosure 140. The conduit pumps functionally associated with peripheral conduit 174 are set to suction mode so that the resulting liquid flow pulls the cell onto cell wall penetrating tool 204, penetrating the cell wall. If it is desired to extract a sample from inside the cell, the conduit pump functionally associated with axial conduit 186 is set to suction mode. If it is desired to inject a reagent into the cell, the conduit pump functionally associated with axial conduit 186 is set to injection mode. As described for cell manipulation element 198, post-penetrating cell release is accomplished by setting conduit pumps functionally associated with peripheral conduit 174 to injection mode so that the resulting liquid flow pushes the penetrated cell off from cell wall penetrating tool 204.

Figure 7I:
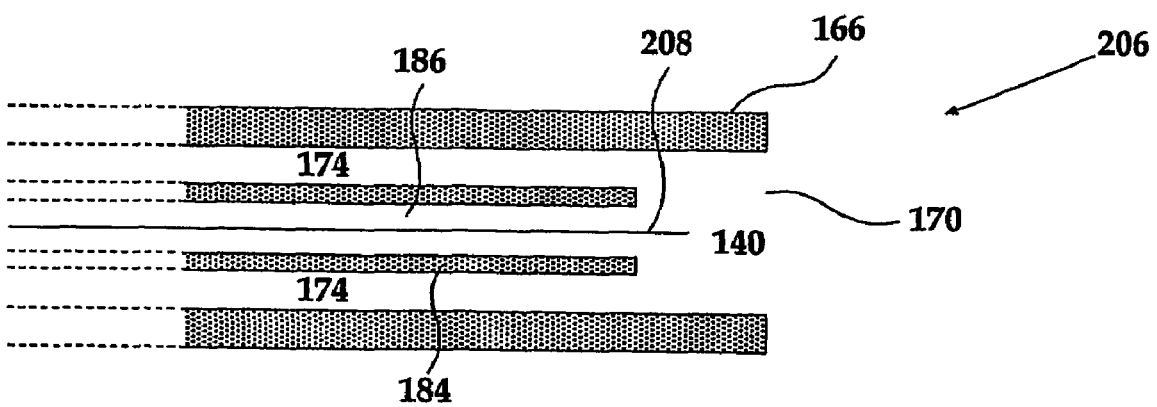
FIG. 7I is a cross section view of a schematic depiction of a preferred embodiment of a cell manipulation element with a retractable cell wall penetrating tool.

An alternative method for releasing a penetrated cell from a cell wall penetrating tool is by providing a cell manipulation element 206 with a retractable cell wall penetrating tool 208 as depicted in FIG. 7I. Cell manipulation element 206 is similar to cell manipulation element 182 excepting that a cell wall penetrating tool 208, a stainless steel wire, is threaded through bore 186. To penetrate the wall of a cell, the cell is brought into trapping enclosure 140. Pumps functionally associated with conduits 174 and 186 are set to suction mode. The resulting attractive force pulls the cell onto cell wall penetrating tool 208, thus penetrating the cell wall. Post-penetrating cell release is accomplished by pulling cell wall penetrating tool 208 outwards from the penetrated cell through bore 186.

Multi-Cell Reaction Element

A multi-cell reaction element, of which only a multi-cell reaction enclosure 150 is depicted in FIG. 6B, is substantially a cell-manipulation element having an open trapping-end and a multi-cell reaction enclosure 150 both large enough to accommodate at least two cells rather than only one cell like a standard cell-manipulation element as described hereinabove. A multi-cell reaction element can be substantially of any of the types of elements discussed hereinabove (especially as related to the number and arrangement of conduits) and is functionally associated with at least one independently controllable conduit pump.

A multi-cell reaction element provides a venue to isolate two or more cells in one place to enable interaction of the two or more cells. Operation of a multi-cell reaction element is analogous to the operation of cell manipulation elements as described above. As depicted in FIG. 6B, at least two cells 142, each isolated in a separate trapping enclosure 140 are moved according to the method of the present invention to trapping enclosures 140 neighboring multi-cell reaction enclosure 150. The at least two cells 142 are expelled from respective trapping enclosures 140 while a conduit pump functionally associated with the multi-cell reaction element is set to suction mode. The resulting forces draw the expelled cells into multi-cell reaction enclosure 150. Inside multi-cell reaction enclosure 150 the at least two cells 142 interact. If desired, reagents are added as described hereinabove and hereinbelow. When the cell interaction is completed the at least two cells 142 are expelled from multi-cell reaction enclosure 150. The at least two cells 142 can be discarded or reisolated in trapping enclosures 140 in the usual way.

Importantly, in a preferred embodiment a cell manipulation probe of the present invention is provided with more than one multi-cell reaction element.

Sample Introduction Element

Figure 6D:
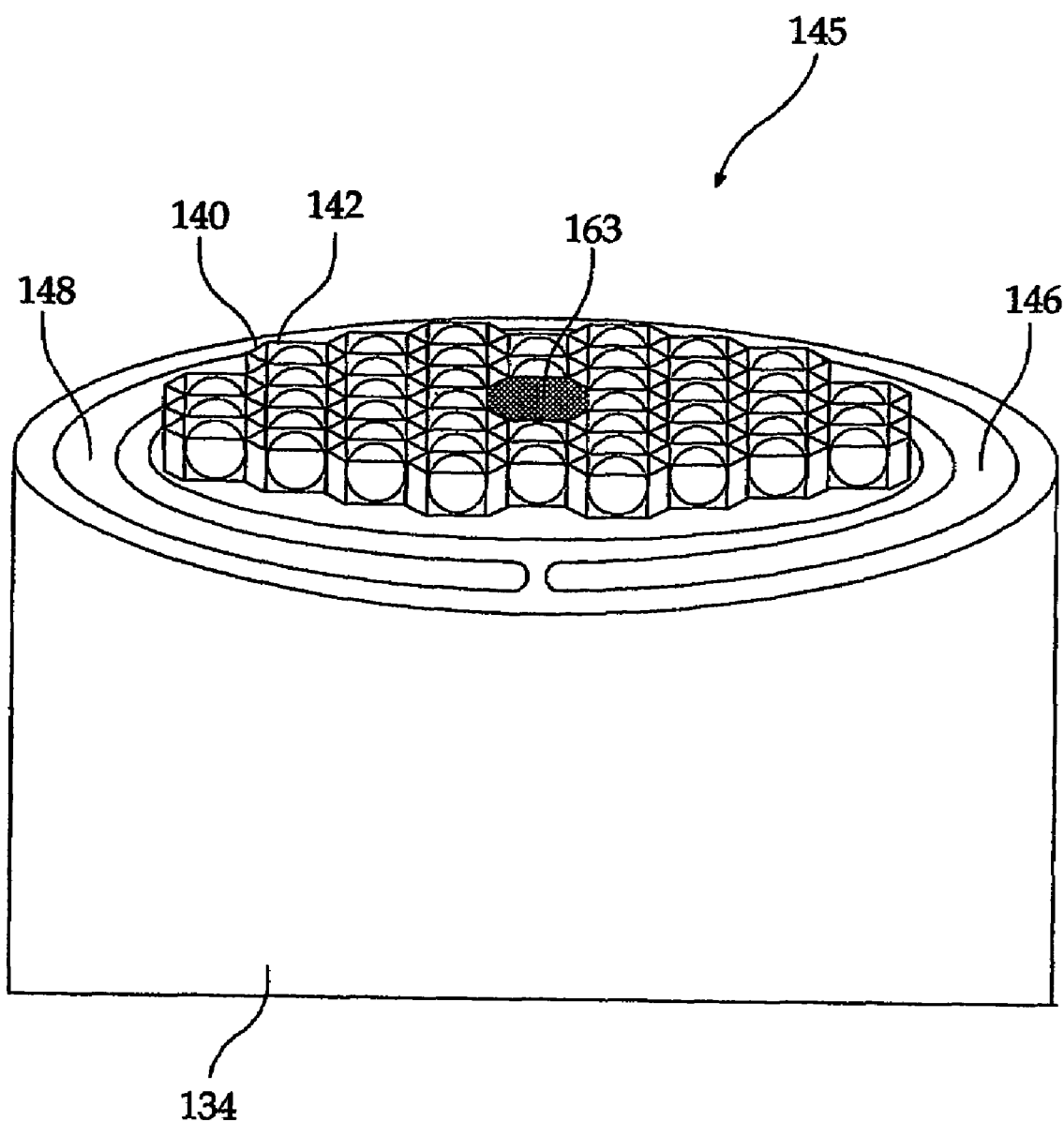
FIG. 6D is a schematic depiction of an alternative embodiment of a probe tip end of a cell manipulation probe.

In FIG. 6D, in the center of matrix 145 emerges the outlet of sample introduction element 163. Sample introduction element is substantially a tube functionally associated with an inlet pump (not depicted). Samples containing cells that are to be manipulated using the device of the present invention are introduced through sample introduction element 163.

Isolation Element

An isolation element, of which only a substantially semicircular isolation inlet 146 is depicted in FIG. 6B, is substantially a multi-cell reaction element with significant structural differences arising from the different uses for which these two elements are intended. An isolation element is primarily intended to provide a location where a user of a device of the present invention concentrates a relatively large number of cells without necessarily intending to later manipulate the cells as individuals. For example, certain cells can be sorted from a large group of cells, and only the certain cells are selected and transferred to an isolation enclosure of the isolation element. From the isolation enclosure the certain cells are removed, either in accordance with the method of the present invention or in some other manner. Therefore, an isolation enclosure that is part of an isolation element is generally large enough to accommodate a relatively large volume of fluid and many cells. At a minimum, isolation element is functionally associated with an isolation pump configured to operate in a suction mode. When the isolation pump is operated, cells are drawn into the isolation enclosure of the isolation element. In some embodiments, an isolation element is functionally associated with an isolation pump configured to operate also in an injection mode. When the isolation pump is operated in injection mode, cells trapped in the isolation enclosure are expelled back to the vicinity of probe tip 134. Preferably, the isolation enclosure of an isolation element is provided with a diaphragm or other valve-like structural feature. A user can, using a needle-equipped syringe (or other appropriate device), draw out cells and fluids isolated in the isolation enclosure.

Importantly, in a preferred embodiment a cell manipulation probe of the present invention is provided with more than one isolation element.

Waste Element

A waste element, of which only a substantially semi-circular waste inlet 148 is depicted in FIG. 6B, is substantially a tubular element functionally associated with a waste pump operable in suction mode. The function of waste element is to remove undesired or not needed substances from the proximity of probe-end 134 of cell-manipulation probe 132, and especially from matrix 145. When a functionally associated waste pump is activated, cells, fluid, cell debris and the like are drawn through waste inlet 148 of the waste element and discarded.

Cell-Manipulation Probe

A cell-manipulation probe of the present invention is composed of at least two but preferably a multiplicity of individual cell-manipulation elements as described above. The cell-manipulation elements are arranged so that the open trapping-ends of the cell-manipulation elements are in functional proximity of each other, that is at a distance and orientation so that cells can be transferred from a first cell-manipulation element to a neighboring cell-manipulation element according to the method of the present invention. Preferably but not necessarily a cell-manipulation probe is also provided with a sample introduction element, waste element, an isolation element and/or a multi-cell reaction element.

In some embodiments, a cell-manipulation probe may be homogenous, that is that all the component cell-manipulation elements are substantially the same. In other embodiments, a cell-manipulation probe is heterogeneous, that is the cell-manipulation probe includes a variety of different cell-manipulation elements. Differences between the cell-manipulation elements making up a heterogeneous cell manipulation probe potentially include the geometry of the trapping enclosures (especially size of the trapping enclosure or size of the open trapping-ends), the number of conduits and the arrangements of conduits. A cell-manipulation probe potentially includes some or all of the types of cell manipulation elements discussed hereinabove, but potentially types of cell-manipulation elements not discussed herein but may arise are also included. The utility of a heterogeneous cell-manipulation probe is discussed hereinbelow.

Figure 8A:
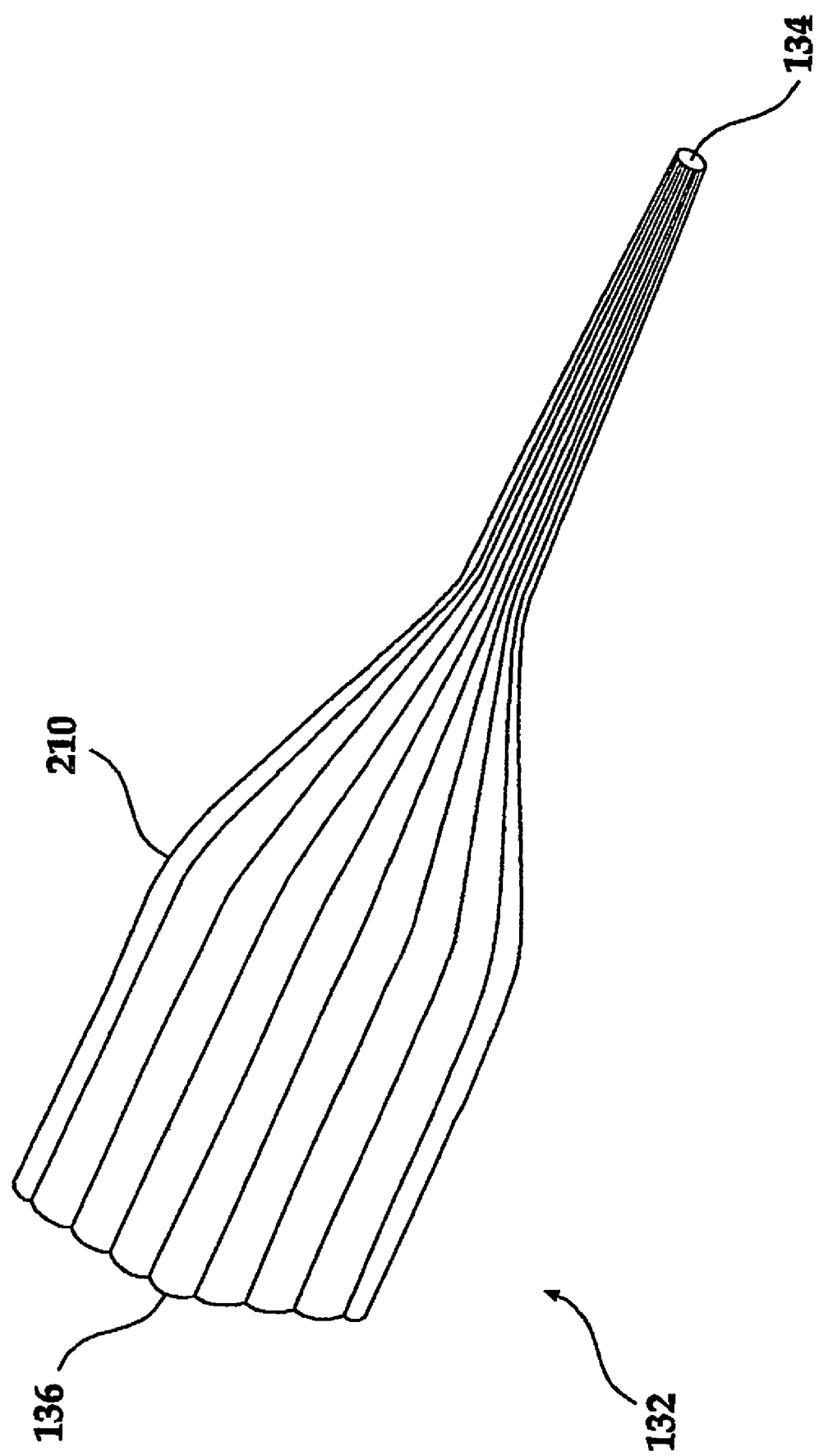
FIG. 8A is a perspective view of a preferred embodiment of a cell manipulation probe.
Figure 8B:
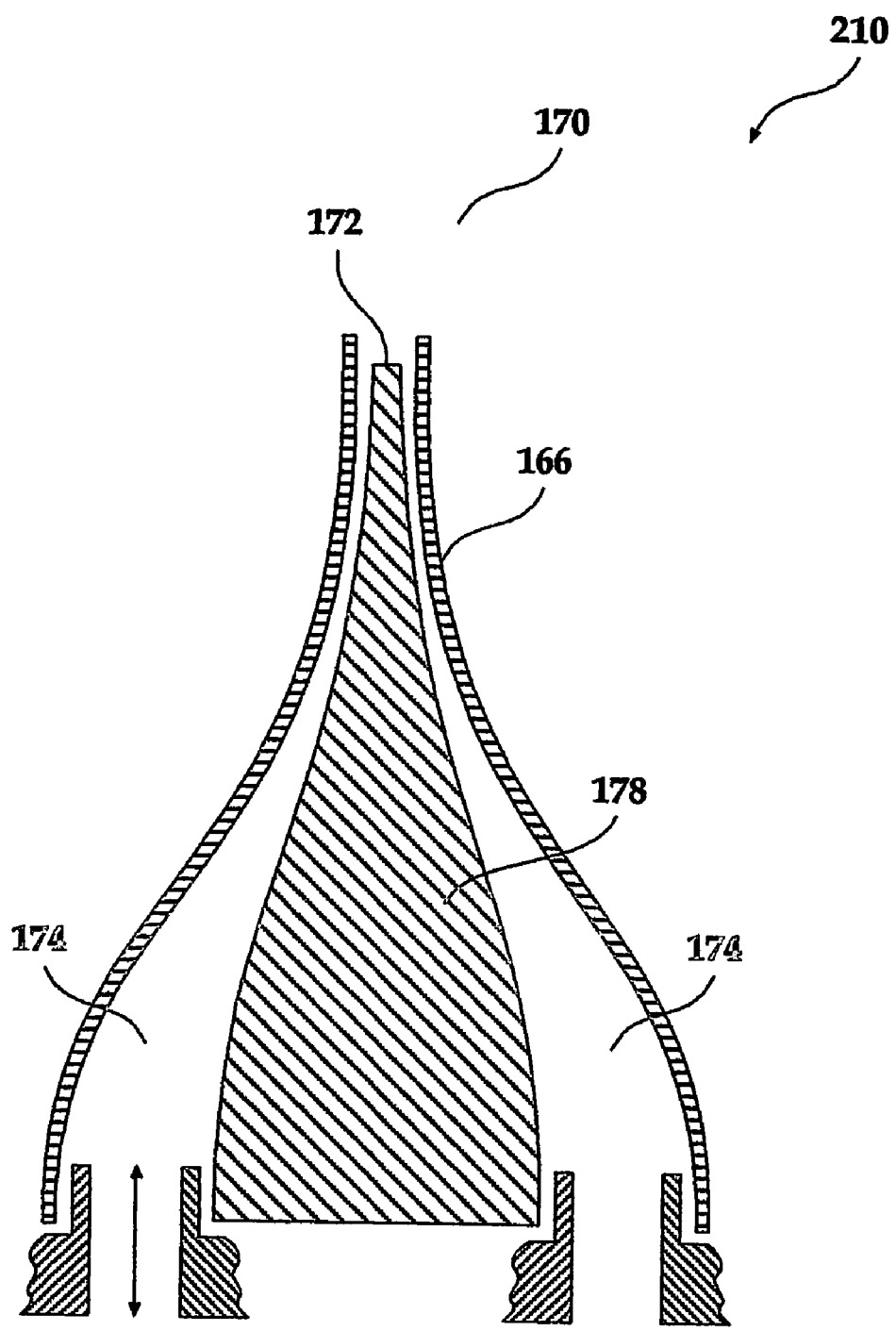
FIG. 8B is a cross section view of a schematic depiction of a preferred embodiment of a cell manipulation element.

In a preferred embodiment, a cell manipulation probe is a bundle of cell manipulation elements. In FIG. 8A a cell manipulation probe 132 is depicted. In FIG. 8B a component cell manipulation element 210 similar to cell manipulation element 176 is depicted in cross section. As seen in FIG. 6A and in FIG. 8A a cell manipulation probe 132 has a probe-end 134 and a butt end 136. As depicted in FIG. 8A, generally speaking, at butt end 136 of cell manipulation probe 132 the ends of the individual cell manipulation elements 210 are relatively large ($\sim 10^3$ microns, 1000 to 2000 microns) so as to allow simple maintenance and attachment of conduits and cell manipulation elements to functionally associated pumps and the like. Generally speaking, at probe-end 134 of cell manipulation probe 132 the ends of individual cell manipulation elements 210 make up a matrix 145 of respective open trapping-ends 140 and have dimensions determined by the uses and size of cells to be manipulated, which are generally significantly smaller in the micron scale, FIG. 6B. For example, the size of open trapping ends for the manipulation of cells is in the order of between $10^{-1}$ to $10^2$ microns. Therefore a typical cell-manipulation element 210 and a typical cell manipulation probe 132 are both of a gradually decreasing dimension from butt-end 136 towards probe-end 134, as depicted in FIG. 8.

Observation Component

Although the device of the present invention can be used to manipulate cells without actually observing any individual cell manipulated, it is generally preferable to observe the cells. Observation is useful, for example, for selecting cells for manipulation, for morphological study, for direct observation of biological processes and to confirm that desired manipulations are performed as desired. It is therefore preferable that a device 130 of the present invention be functionally provided with an observation component 150, as depicted in FIG. 6A.

Many different types of observation components can be usefully coupled to a device of the present invention, but preferably an observation component is an optical inspection device. Optical inspection devices such as optical or CCD microscopes having a magnification appropriate for viewing living cells in sizes in the order of $10^{-1}$ microns are known and are commercially available.

As is known to one skilled in the art, an optical or CCD microscope is most effective for the morphological and morphometric characterization of a studied object. It is therefore advantageous to provide a device of the present invention, such as device 130, with an observation component suited for the detection of fluorescence. It is known to one skilled in the art that the measurement of vital fluorescence parameters (fluorescence intensity, polarization, energy transfer) provides important information about a living cell.

Central Control Unit

To allow performance of complex experiments it is preferred that a device of the present invention such as 130 be provided with a central control unit 144 as depicted in FIG. 6A. A typical central control unit such as 144 receives commands from a user through a user input interface 146 and activates pumps 142, observation component 150 and other components as necessary. As is clear to one skilled in the art, a central control unit 144 can advantageously be implemented using a programmable computer.

As is discussed herein, central control unit 144 is also used to determine the exact sequence of activation of pumps 142 and other components of a device 130 of the present invention to trap, move, observe and otherwise manipulate cells using a cell-manipulation probe 132.

In a preferred embodiment, a central control unit 144 is used also to store a record of the experiments and conditions to which each cell was exposed, vide infra.

Although identification, examination and determination of various states of a cell can be performed by a human operator looking at video output produced by an observation component of a device of the present invention, it is preferred that some or all of these functions be performed by a central control unit. Automated image analysis useful in identifying locations of cells and various morphologies is well-known and can be implemented in the context of a device of the present invention using a central control unit by one skilled in the art of image analysis.

Many other functions required from or possible with a central control unit are known or obvious and will not be listed or discussed herein.

Construction of a Cell Manipulation Device

There are many technologies available allowing one skilled in the art to construct a cell manipulation probe of the present invention.

One preferred method for the construction of a cell-manipulation probe of the present invention is free-form manufacturing (FFM) using ceramic powders. As is known to one skilled in the art, in free-form manufacturing a part, such as a cell-manipulation probe, is built "from the ground up" by sequentially dispensing layers of ceramic powder one on top of the other, see for example, U.S. Pat. No. 6,376,148; U.S. Pat. No. 6,238,614; U.S. Pat. No. 6,228,437; U.S. Pat. No. 6,066,285; U.S. Pat. No. 6,117,612; U.S. Pat. No. 6,046,426; U.S. Pat. No. 5,059,266; U.S. Pat. No. 5,204,055 or U.S. Pat. No. 6,206,672. A review of the state of the art of FFM can be found in U.S. Pat. No. 6,376,148, which is incorporated herein by reference for all purposes as if fully set forth herein. It is important to note that when a ceramic powder is used it is generally preferable to use a ceramic powder with as small a diameter as possible, for example 10 nanometer diameter ceramic powders. Since the use of free-form manufacture methods to construct a complex structure such as a cell-manipulation probe of the present invention is known to one skilled in the art, this is not further discussed herein.

A cell manipulation probe, such as cell manipulation probe 132 can be purchased from commercial suppliers, for example from TEGS Ltd. (Saratov, Russia).

A preferred method for the construction of a cell-manipulation probe, such as cell manipulation probe 132, is through the bundling of a multiplicity of glass tubes and rods. Generally speaking, the preferred method involves three steps. In a first step, glass rods and tubes are bundled together in an appropriate way to assemble an incipient cell-manipulation element or, preferably, an incipient cell-manipulation probe. The diameter of the tubes and rods is chosen so that subsequent attachment of pumps and the like to the butt end of the cell-manipulation probe is simple. In a second step, glass rods are fused together. In a third step, one end of the bundle of glass rods and tubes is drawn in the usual manner known to one skilled in the art of glass-working so as to form the probe-end of the cell manipulation probe. In such a way, the size of the probe-end of the cell-manipulation probe is reduced without blocking channels and conduits, producing a cell-manipulation probe as depicted in FIG. 8A.

The method of use of glass tubes and rods in constructing an individual cell-manipulation element is described in further detail with reference to FIG. 9. Extension of the method of arranging glass tubes and rods to the construction of a cell-manipulation probe involves the construction of a multiplicity of cell-manipulation elements and is clear to one skilled in the art upon study of the disclosure herein.

FIG. 9A is a top view of a bundle of seven glass rods 212a, 212b, 212c, 212d, 212e, 212f and 212g used in the assembly of a cell manipulation element whereas FIG. 9B is a vertical cross section of the bundle through the plane A-A. The bundle of seven glass rods 212 can be considered to be an incipient cell-manipulation element 213. It is seen in FIG. 9B that the end of central glass rod, 212g is lower than the end of glass rods 212e and 212c. In fact, the ends of all six glass rods 212a through 212f are at the same height. The volume in incipient cell manipulation element 213 defined by the sides of glass rods 212a through 212f and the top end of recessed glass rod 212g corresponds to the trapping enclosure of the ultimately fashioned cell manipulation element. The top end of recessed glass rod 212g corresponds to the cell stop of the ultimately fashioned cell-manipulation element. The interstitial volumes between seven glass rods 212 correspond to six fluid passages that become the conduit or conduits in the ultimately fashioned cell-manipulation element.

The use of seven glass rods 212 as depicted in FIGS. 9A and 9B and as described hereinabove allows the construction of a cell-manipulation element such as 176 of FIG. 7B, 188 of FIG. 7E, 198 of 7G and 206 of 7I, although for the construction of cell manipulation elements such as 198, a glass rod having a stainless steel wire through the central axis may replace glass rod 212g. It is important to note that generally the differentiation between a single conduit cell-manipulation element such as 176 and a multiple conduit cell-manipulation element such as 188, 198 or 206 is not necessarily apparent in the incipient cell-manipulation element 213. Rather, after the incipient cell-manipulation element (or incipient cell-manipulation probe) is drawn, the exact nature of the ultimately fashioned cell-manipulation element is determined by how functionally associated conduit pumps are attached to the passages. If all six passages are connected to a single conduit pump, then a cell-manipulation element having one conduit such as 188 is formed. If two adjacent liquid passages are connected to one conduit pump, whereas the opposing pair of liquid passages is connected to a second conduit pump then a cell manipulation element having two peripheral conduits such as 188, 198 or 206 is formed.

In FIG. 9C a method of construction for a cell manipulation elements such as 182 of FIG. 7D, 202 of 7H or 206 of 7I is depicted. Analogously to the method described immediately hereinabove and depicted in FIG. 9A and FIG. 9B, six glass rods 212a, 212b, 212c, 212d, 212e and 212f are arrayed about a glass tube 214. Since the end of glass tube 214 is lower than the ends of glass rods 212, the volume defined by the sides of glass rods 212a through 212f and the top end of recessed glass tube 214 corresponds to the trapping enclosure of the ultimately fashioned cell manipulation element. The top end of recessed glass tube 214 corresponds to the cell stop of the ultimately fashioned cell-manipulation element. The interstitial volumes between six glass rods 212 and recessed glass tube 214 correspond to six passages that potentially become conduits in the ultimately fashioned cell-manipulation element. The hollow bore of recessed glass tube 214 corresponds to the axial conduit in the ultimately fashioned cell-manipulation element. To fashion a cell wall penetrating tool 204 of a cell manipulation element 202, the end of recessed glass tube 214 is sharpened.

It is clear to one skilled in the art upon studying the description herein, that in order to fashion an incipient cell-manipulation probe instead of an incipient cell manipulation probe, more than seven glass rods and tubes are bundled together. It is also clear to one skilled in the art upon reading the description herein that other types of cell manipulating elements or other elements for constructing a cell manipulating probe such as a waste element or an isolation element can be produced in an analogous fashion to that described hereinabove.

As stated above, once chosen the glass rods and tubes making up an incipient cell-manipulation element or incipient cell manipulation probe are bundled together in an appropriate fashion, the rods and tubes are fused together. Thereafter, the appropriate end of the incipient cell-manipulation element or incipient cell manipulation probe is drawn out into the shape depicted in FIG. 8A to make a cell manipulation element or cell manipulation probe, respectively.

In an alternative embodiment, modular cell manipulation elements are made and assembled to make a cell manipulation probe. In FIG. 10 are depicted examples of modular cell manipulation elements.

Figure 10A:
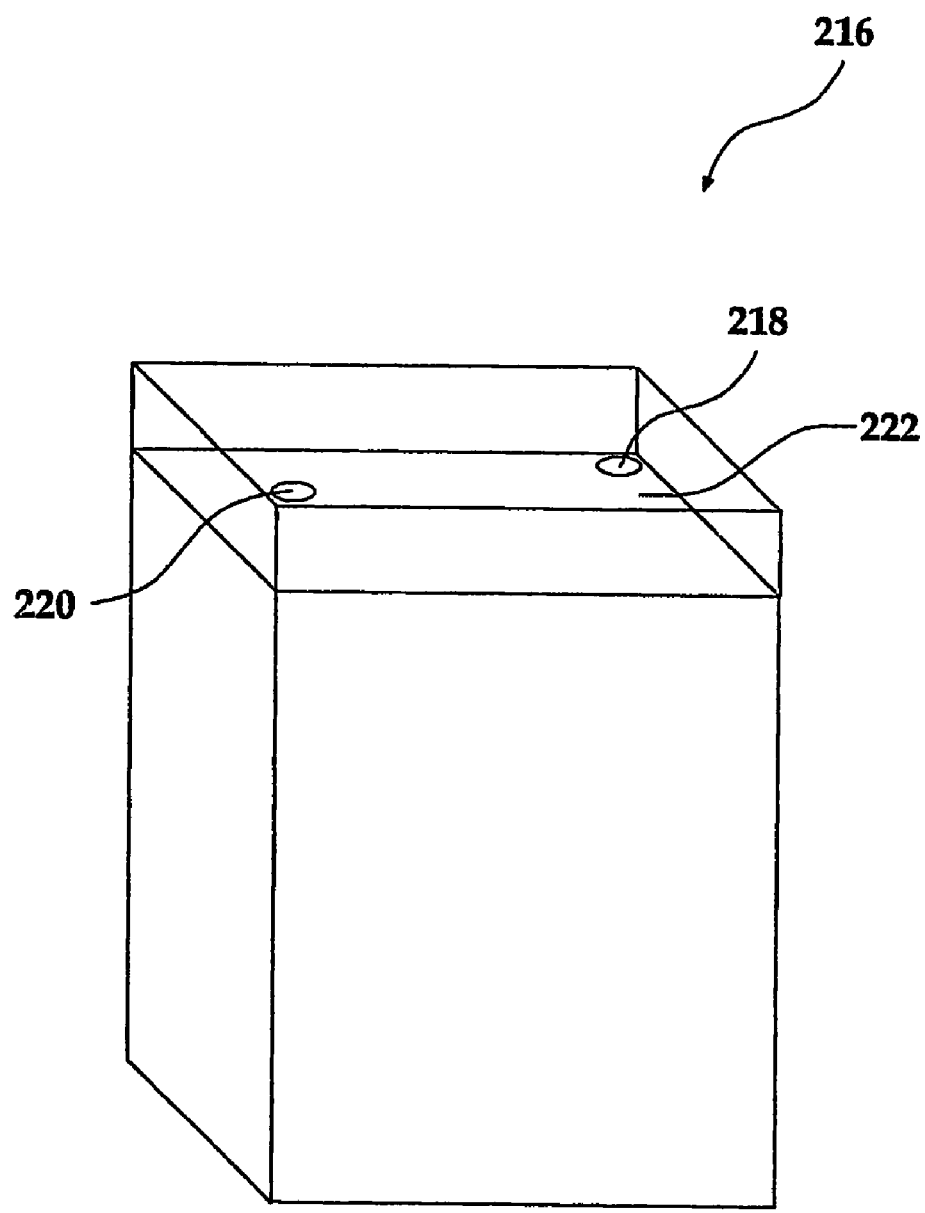
FIGS. 10A-10C are perspective views of modular cell manipulation elements.
Figure 10B:
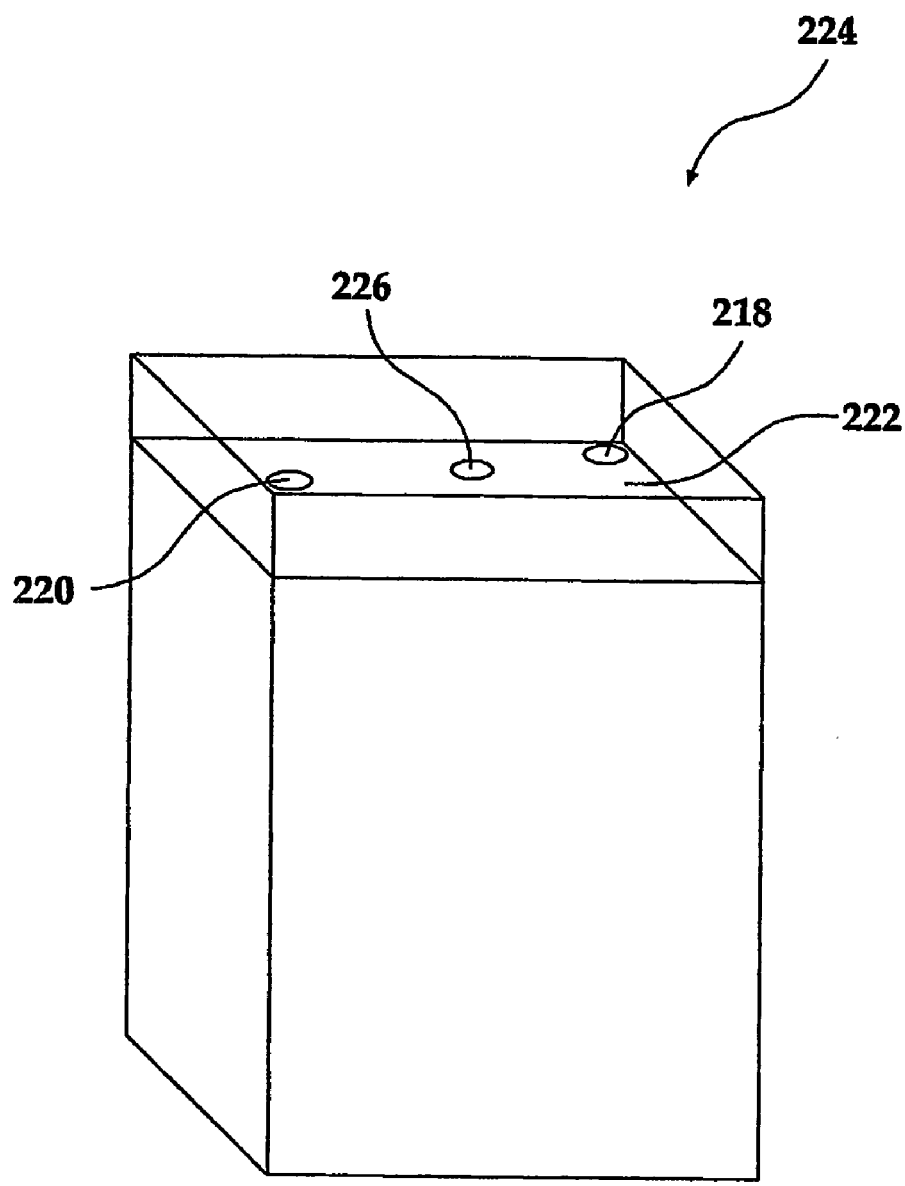
Figure 10C:
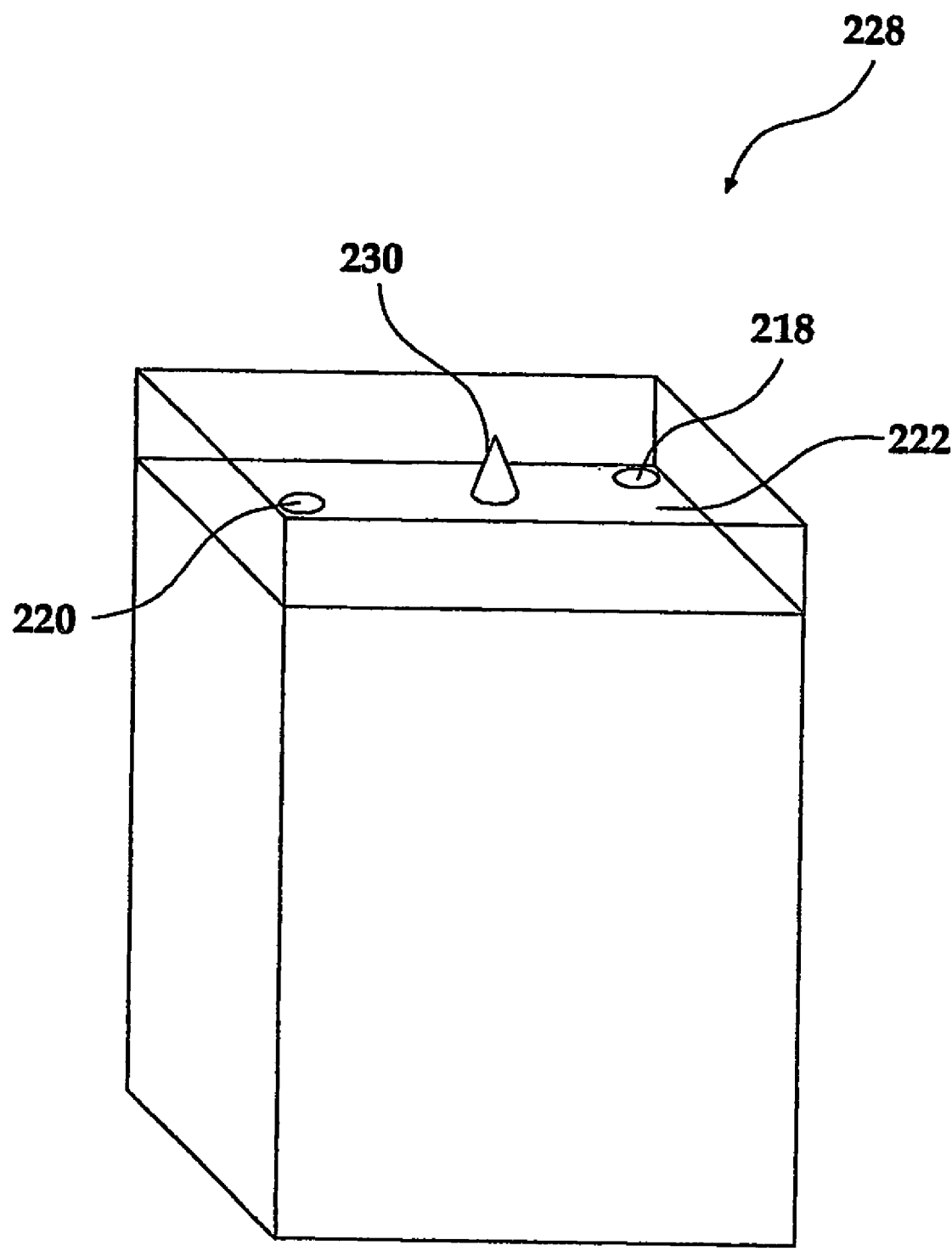

In FIG. 10A is depicted one embodiment of a simple modular cell manipulation element 216 with two conduits, 218 and 220. The horizontal cross-section of cell manipulation element 216 is substantially square. It is important to note that other embodiments of similar cell manipulation elements potentially have non-square cross-sections. Conduits 218 and 220 function analogously to conduits described hereinabove. Illustrative but non-limiting dimension of cell manipulation element 216 are a height of 1000 micron, a width of 20 micron and a depth of 20 micron. The top of cell manipulation element 216 is recessed, creating a well-like enclosure, 222 serving as a dimple or trapping enclosure as described hereinabove. An illustrative but non-limiting depth of well-like enclosure 222 is 10 micron. Other types of elements, especially cell manipulation elements, can be conceived for use together with modular cell manipulation elements such as 216. Examples of such other types of elements include a modular cell manipulation element 224 with three conduits 218, 220, and 226, depicted in FIG. 10B and a modular cell manipulation element 228 with two conduits 218 and 220 and a cell wall penetrating tool 230, depicted in FIG. 10C.

Figure 10D:
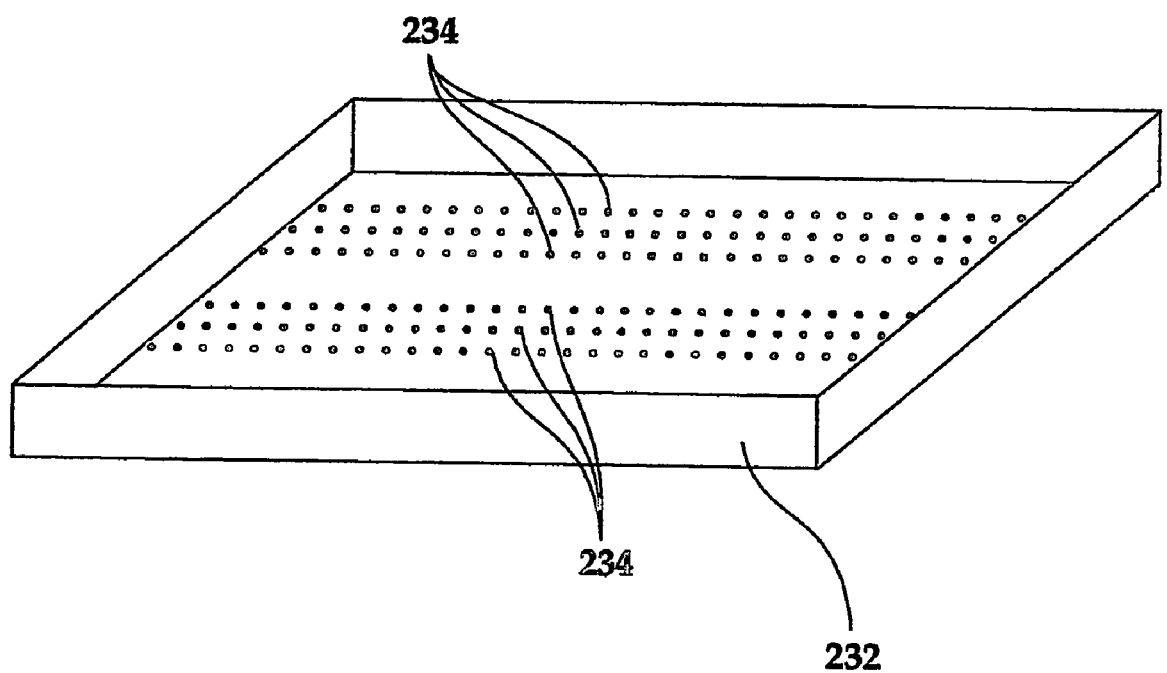
FIG. 10D is a perspective view of an assembly plate used in conjunction with modular cell manipulation elements to make a cell manipulation probe.

Assembly of a cell manipulation probe from modular cell manipulation elements such as 216, 224 and 228 is done by providing an assembly plate 232, depicted in FIG. 10D. Assembly plate 232 is a monolithic structure having a multiplicity of pin connector triplets 234, which fit into the bottom openings of conduits 218, 220 and 226 or a conduit of cell wall piecing tool 230 of modular cell manipulation elements 216, 224 and 228. At the bottom of assembly plate 224, each pin connector 226 is connected to fluid lines (not depicted), which connect to functionally associated conduit pumps (not depicted). Thus a multiplicity of modular cell manipulation elements 216 can be disposed in exact juxtaposition on assembly plate 224, thus providing functionally associated conduit pumps to cause fluid to flow through conduits 218 and 220.

The various components necessary for implementing a cell manipulation probe using modular cell manipulation elements, including modular cell manipulation elements can be purchased from commercial suppliers, for example from TEGS Ltd. (Saratov, Russia).

Once a cell-manipulation probe is constructed, the assembly of a device of the present invention from commercially available components is well within the ability of one skilled in the art upon study of the description herein.

Suitable computers, software and related peripheral equipment for implementing a central control unit are available from International Business Machines Corporation (Armonk, N.Y., USA). Any required unique or dedicated software can be written by one skilled in the art of computer programming.

Suitable CCD microscopes for implementation of an observation component are available, for example, from Hirox Co Ltd. (Suginami-Ku, Tokyo, Japan).

Flow-generators and peripheral equipment suitable for implementing the present invention are available from, for example, GeSIM (Grosserkmannsdorf, Germany) or Fluidigm Corporation (San Francisco, Calif., USA).

Steps Used in Building Experiments

A device such as 130 depicted in FIG. 6 designed for manipulating individual cells found in a liquid medium (especially a cell culture medium) and allows performance of many novel and useful experiments. Experiments are done by performing a series of one or more steps (also termed manipulations or functions). A few standard steps that are useful building blocks for various experiments are described in detail hereinbelow with reference to device 130 as depicted in FIG. 6 and especially with reference to FIG. 6B. Unless otherwise stated, for the examples below it is assumed that all cell manipulation elements are similar to cell manipulation element 182 depicted in FIG. 7D with a reagent inlet system such as depicted in FIG. 7F.

Useful steps, manipulations and functions include loading and isolating of a cell in a trapping enclosure, washing a cell, suspending a cell for observation, penetrating a cell wall (e.g. for removing a sample or inoculation with a reagent), exposure of a cell to a reagent, allowing a cell to interact with other cells, select a cell, sort cells and separate types of cells from others.

Cell Loading and Isolating

Generally but not necessarily, a first step in an experiment is the loading of cells into trapping enclosures 140 of device 130.

Sample inlet pump 158 receives a command from central control unit 144 to operate, loading a sample of cell-containing liquid through sample inlet 152 onto matrix 145 on probe-end 134 of cell manipulation probe 132, FIG. 6C. In an alternate embodiment using the variant of cell manipulation probe 145 depicted in FIG. 6D, a cell-containing sample is introduced through sample introduction element 163 and flows out onto matrix 145.

For all trapping enclosures 140 in which it is desired to load cells 142, a functionally associated first conduit pump 190 and a second conduit pump 192 are set by central control device 144 to suction mode. A cell 142 in proximity of a respective open trapping-end 170 is drawn into a respective trapping enclosure 140 and is drawn into a trapping enclosure 140 until making contact with a respective cell-stop 184.

After a certain period of time when it is estimated that cells are trapped in all desired trapping enclosures 140, associated first conduit pumps 190 and second conduit pumps 192 are set to inactive mode by central control device 144. Observation component 150 receives a command from central control element 144 to examine all trapping enclosures 140 to ascertain if cells 142 are trapped therein. First conduit pump 190 and second conduit pump 192 of trapping enclosures 140 that are empty are again set to suction mode until all desired trapping enclosures 140 hold cells 142.

Once cells 142 are held in all desired trapping enclosures 140, a waste pump functionally associated with a waste element is set to suction mode by central control unit 144. Excess cells and liquids not trapped in trapping enclosures 140 are removed and disposed of through inlet 148 of the waste element. Subsequently, fluid inlet pump 160 is activated to dispense an appropriate cell culture medium through fluid inlet 154 onto matrix 145 by central control unit 144.

In one embodiment, it is desired that cells 142 be trapped in substantially all trapping enclosures 140. In such an embodiment, first conduit pumps 190 and second conduit pumps 192 associated with all trapping enclosures 140 are set to suction mode and consequently draw cells 142 into a respective trapping enclosure 140.

In a different embodiment, it is desired to maintain a maximal flexibility for movement of cells 142. In such an embodiment, in a first step first conduit pumps 190 and second conduit pumps 192 associated with only non-neighboring trapping enclosures 140 are set to suction mode. In subsequent steps cells can be moved and transferred between trapping enclosures with great ease as every cell 142 has a free path to every trapping enclosure 140 of matrix 145, vide infra.

Cell Observation

In one embodiment of the present invention, a cell 142 in a trapping enclosure 140 is observed through a respective open trapping-end 170. In another embodiment, the walls of a trapping enclosure 140 are transparent and a cell 142 held therein is observed therethrough.

In a preferred embodiment, when cell manipulation elements are provided with a conduit or trapping enclosure deep enough to allow deep cell entry, cells 142 not to be observed are drawn inside the cell manipulation element so that only one or only a few cells 142, each in a trapping enclosure 140, remain in the proximity of a respective open trapping-end. Observation is then performed only on those cells 142 in proximity of a respective open trapping-end 170.

Most preferably, if a cell 142 is held in a trapping enclosure 140 of a cell manipulation element suitable for suspending cell 142 above the trapping enclosure using the Venturi effect (such as cell manipulation element 182), as described above, then cell 142 to be observed is suspended for observation. Central control unit 144 sets a conduit pump functionally associated with axial conduit 186 to injection mode while conduit pumps functionally associated with one or more peripheral conduits 174 are set to suction mode. As discussed hereinabove, cell 142 trapped in trapping enclosure 140 is elevated out of trapping enclosure 140 and suspended thereabove. The advantages of suspending a cell 142 to be observed in such a way are manifold. Cell 142 can be selectively and intensely illuminated using incoherent and/or coherent light aimed at cell 142. Light scattering and shadows are eliminated. Importantly the greater intensity of light allows the use of a small camera aperture, increasing depth of field and leading to the recording of a sharper image. Further, the intensity of lighting can be chosen to maximize contrast and thus maximize the observable details.

After cell 142 is examined, associated first conduit pump 190 and second conduit pump 192 may be both set to suction mode to return cell 142 to trapping enclosure 140. Thereafter an additional cell can be examined if required.

Reagent Addition Through Vial Reagent Inlet

One way to expose cells to reagents is through a vial reagent inlet 156. Central control unit 144 activates vial reagent inlet pump 162 to dispense an amount of a reagent through a vial reagent inlet 156 onto matrix 145. However, in order for a cell 142 held in a trapping enclosure 140 to come in contact with a thus-dispensed reagent, the reagent must be brought into trapping enclosure 140.

If all cells in all trapping enclosures are to be exposed to the reagent (for example, in the case where the reagent is a nutrient or a fluorescent marker), then one or both conduit pumps 190 and 192 associated with all trapping enclosures 140 are set to suction mode, drawing an amount of reagent into each trapping enclosure 140.

If, however, it is desired that only certain cells 142 be exposed to a given reagent, then one or both conduit pumps 190 and 192 functionally associated only with the respective trapping enclosures 140 of certain cells 142 are set to suction mode.

Reagent Addition Through a Cell-Manipulation Component

As stated above, the fact that a given trapping enclosure 140 is functionally associated with two independently controllable conduit pumps 190 and 192 allows "washing" of trapping enclosure 140 or of a cell 142 held within trapping enclosure 140 by using one functionally associated conduit pump to inject a washing liquid simultaneously with extraction of the washing liquid using the other conduit pump.

As stated above, the fact that a trapping enclosure 140 is functionally associated with two independently controlled conduit pumps 190 and 192 together with a reagent injection pump 194 as depicted in FIG. 7F allows selective exposure of a cell 142 in trapping enclosure 140 to a reagent. Reagent injection pump 194 is set to add a desired amount of reagent to the flow produced by first conduit pump 190 is set to injection mode. The flow of fluid from conduit 174 carries reagent to trapping enclosure 140, thus exposing cell 142 to the reagent. To prevent leakage of the reagent out of trapping enclosure 140, second conduit pump 192 is set to suction mode, actively removing reagent and other fluids from enclosure 140.

Moving a Cell to a Different Trapping Enclosure

The movement of a cell 142 held in a trapping enclosure 140 to another trapping enclosure by a series of transfers between neighboring trapping enclosures is performed according to the method of the present invention and is clear from the description hereinabove. Such a transfer is schematically depicted in FIG. 11.

Figure 11A:
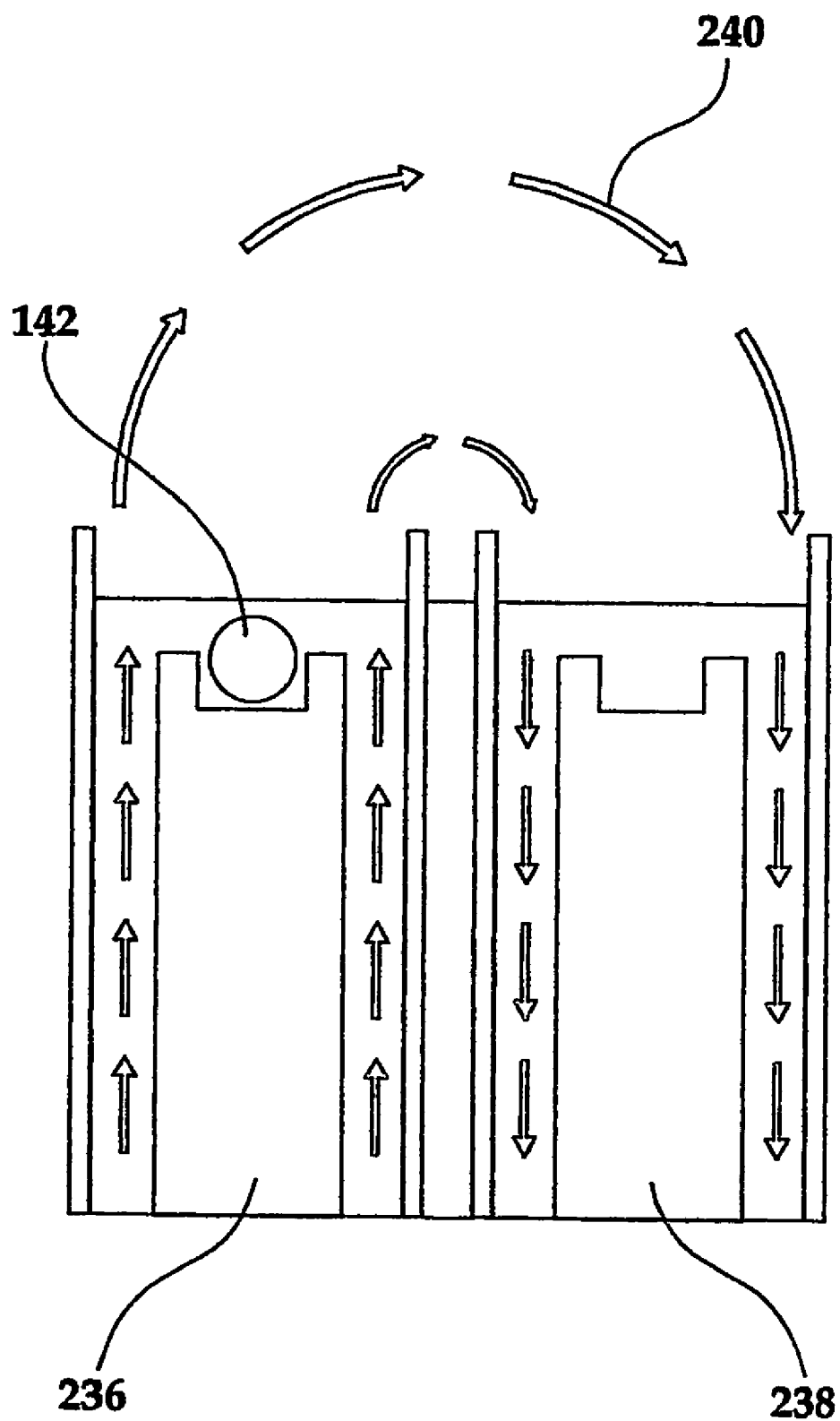
FIGS. 11A-11C illustrate the transfer of a cell from one cell manipulation element to a neighboring cell manipulation element.

A cell 142 is held in a trapping enclosure of cell manipulation element 236, FIG. 11A.

Figure 1A:
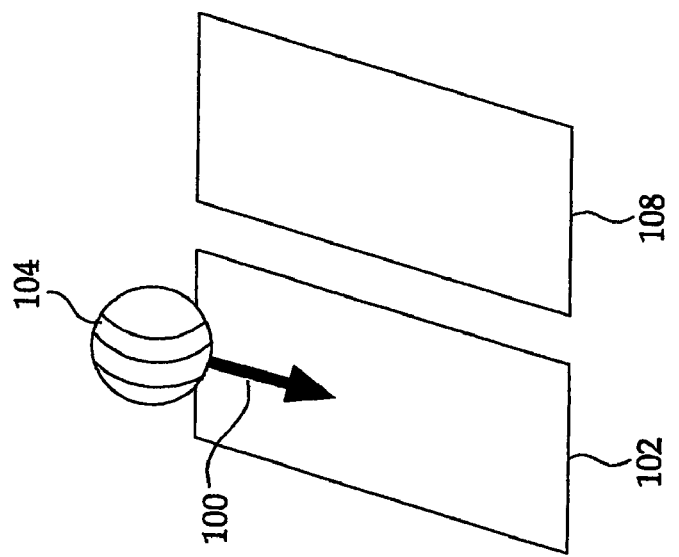

As depicted in FIG. 1A, conduit pumps functionally associated with cell manipulation element 236 are set to injection mode and conduit pumps functionally associated with neighboring cell manipulation element 238 are set to suction mode. A flow of liquid is produced from cell manipulation element 236 to neighboring cell manipulation element 238, depicted as arrows 240.

Figure 11B:
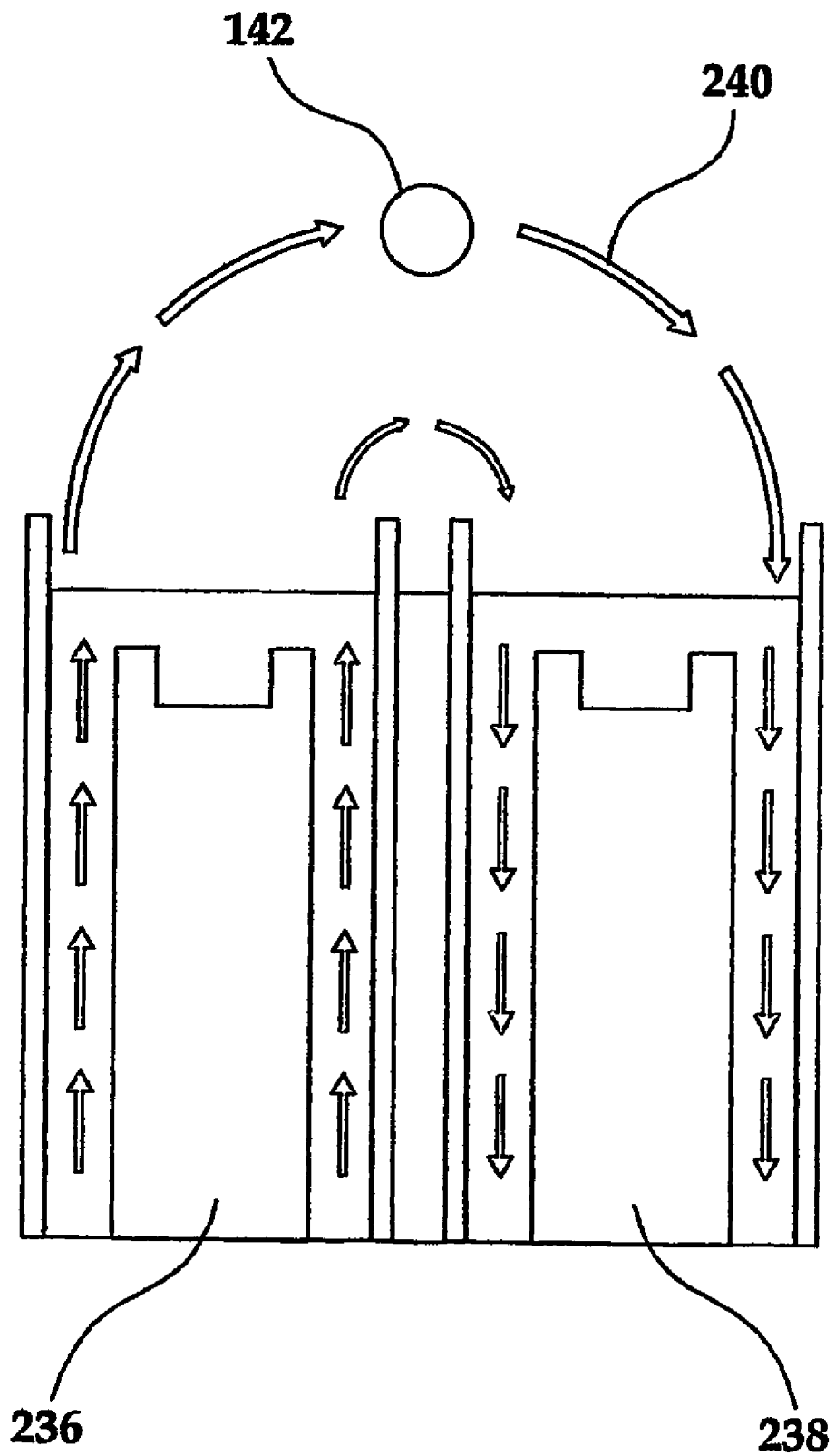

As depicted in FIG. 11B, the force produced by flow of liquid 240 ejects cell 142 from cell manipulation element 236 and carries cell 142 towards neighboring cell manipulation element 238.

Figure 11C:
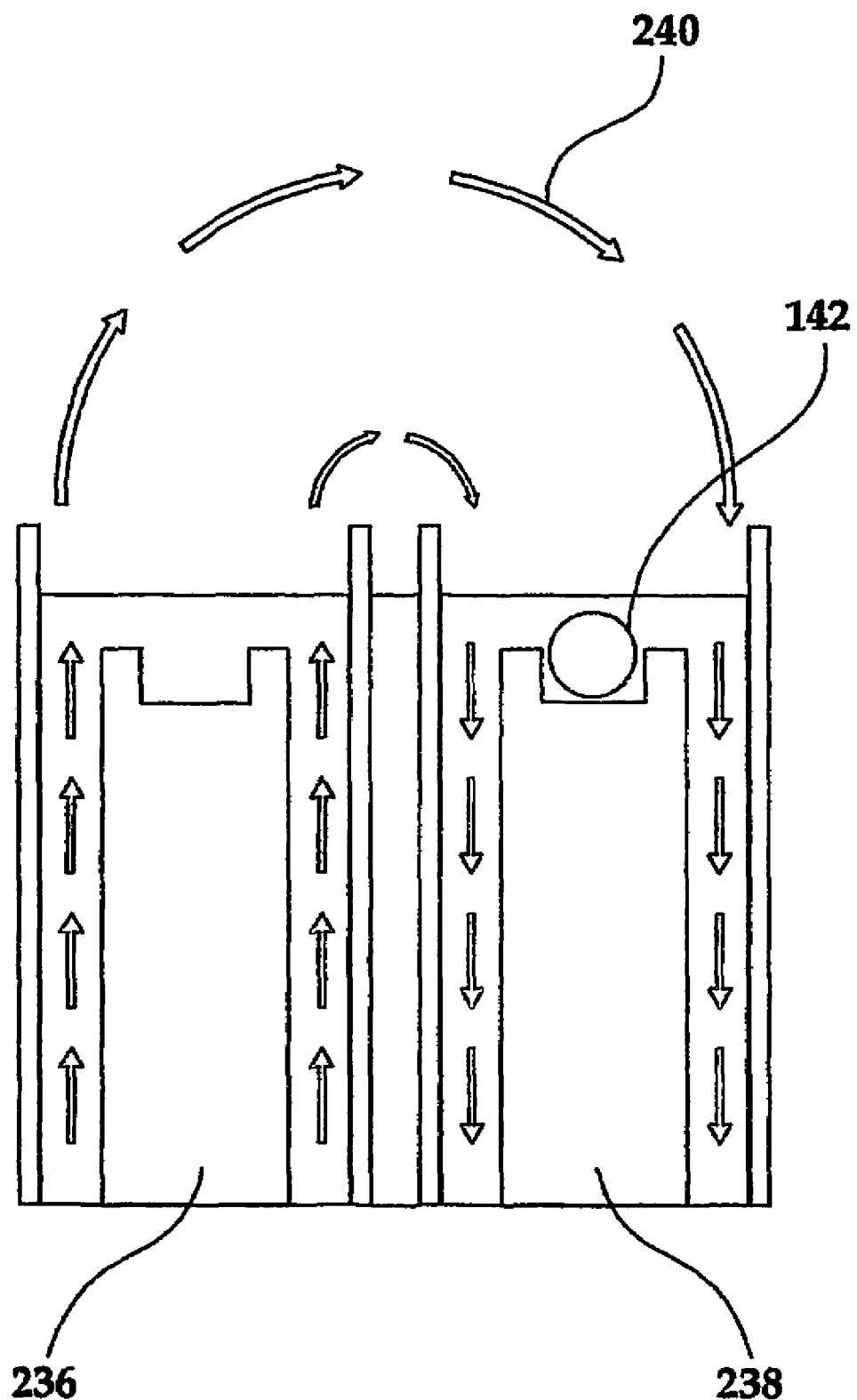

As depicted in FIG. 11C, cell 142 is ultimately carried into the trapping enclosure of neighboring cell manipulation element 238.

A cell is moved from any trapping enclosure to any other unoccupied trapping enclosure along a path defined by a series of unoccupied neighboring enclosure, according to the method of the present invention and as described herein and in FIG. 3. The ability to move an individual cell from one trapping enclosure to any other trapping enclosure allows the performance of many useful experiments.

For example, it may be desirous to expose similar cells to a series of reagents, but to compare the effect of changing the order of exposure or the length of time a cell is exposed to a given reagent. To perform such an experiment, cells are loaded into trapping enclosures. The cells are sequentially transported to different trapping enclosures provided with specific reagents and therein exposed to reagents, as required.

It is also often desired to study the interaction of two different types of cells. Cells of a first type are loaded into trapping enclosures, preferably unoccupied trapping enclosures. Cells of a second type are loaded into other trapping enclosures, preferably unoccupied trapping enclosures. A cell of each type is moved, as described above, to a multi-cell reaction enclosure 151. In another embodiment contingent on a properly sized trapping enclosure, a first cell is moved into a trapping enclosure already occupied by a second cell. Observation component 150 is used to observe any interaction. When desired, the two cells are ejected from multi-cell reaction enclosure 151 and another pair of cells is loaded therein for study.

It is also often desired to move a specific cell or cells held in a trapping enclosure to an isolation element in order to collect cells of a certain type for further study. Each individual cell is transferred through a series of trapping enclosures, from one trapping enclosure to a neighboring trapping enclosure, until cell is located in a trapping enclosure 140 neighboring an isolation inlet 146 of an isolation element. The cell is ejected from trapping enclosure 140 while a conduit pump functionally associated with the isolation element is activated so as to draw cell 142 into the isolation element through isolation inlet 146.

Analogously, it may also be desired to discard a specific cell 142 from a trapping enclosure. Cell 142 is transferred from one trapping enclosure 140 to a neighboring trapping enclosure 140 until cell 142 is located in the vicinity of waste inlet 148. Cell 142 is ejected from trapping enclosure 140 while a pump functionally associated with the waste element is activated so as to draw cell 142 through waste inlet 148.

In most embodiments of the present invention, a device 130 is configured to allow simultaneous activation of many pumps and thus perform manipulations and functions simultaneously. Thus, in one embodiment of the present invention, numerous cells are individually manipulated simultaneously using one device of the present invention such as 130. Thus, in another embodiment of the present invention, numerous cell-cell interactions are simultaneously performed using one device of the present invention such as 130. In another embodiment, numerous specific treatments and manipulations of numerous individual cells are simultaneously performed using one device of the present invention such as 130. In another embodiment, many cells are simultaneously moved from a first trapping enclosure to another trapping enclosure, as desired. The preparation of an algorithm that calculates an optimal series of steps, where in each step one or more cells 142 are transferred from one trapping enclosure 140 to another, is well within the ability of one skilled in the art of computer programming. Such an algorithm is easily implemented in central control unit 144 of a device 130 of the present invention. Once an optimal series of steps is found, central control unit 144 sets the various conduit pumps to perform the appropriate actions according to the calculated series of steps so as to relocate and rearrange cells 142 as required.

Preferably, at any given moment, the locations of all cells 142 in trapping enclosures 140 of a cell manipulation probe 132 are recorded in central control unit 144. Preferably, central control unit 144 also keeps a record of the manipulations that any given cell has undergone. In such a way, data can be easily analyzed.

EXEMPLARY EXPERIMENTS

One skilled in the art, upon perusal of the description of the present invention hereinabove is able to construct a device of the present invention and to plan a plethora of heretofore-impossible experiments, manipulations and studies that yield hitherto unavailable scientific information. For simplicity, the words experiment, manipulation and study will be used hereinbelow interchangeably. The manipulation of individual cells enabled by the teachings of the present invention provides far more information for the understanding of biological implications of phenomena under study compared to bulk studies (e.g., using cuvettes or microplates), flow-through cytometry studies or static cytometry studies.

According to a preferred embodiment of the present invention, specific cells are selected for real-time high-throughput study. It is important to note that some of the studies performed using the teachings of the present invention including some of those described hereinbelow may have been previously manually performed. It is important to note, however, that the teachings of the present invention are the first that allow the performance of such studies automatically on many cells simultaneously as opposed to manually by highly skilled individuals.

An additional advantage of the present invention is that selected cells can be maintained for a relatively long period of time in various environments, allowing a single cell to be used for many different experiments. For instance, using a device of the present invention a large number of cells is exposed to a stimulus and cells that respond to the stimulus in a certain way are isolated, for example, in trapping enclosures of a cell manipulation probe or by transfer to an isolation element as described above. Thereafter, the reaction of the isolated cells to other stimuli can be studied. In summary, once a cell having unusual or otherwise interesting properties is identified the teachings of the present invention are used to isolate and further manipulate the cell, thereby pinpointing an investigation to a subgroup of relevant cells, reducing investigation time and saving valuable resources. Additionally, since such an investigation is done on a cell-by-cell basis, better and more precise data is obtainable, for example, for increased diagnostic accuracy.

The teachings of the present invention can also be used for sorting cells or selecting specific cells from a large population of cells. Such procedures include the selective removal of undesired cells or the harvesting of desired cells found in small proportions from amongst other cells, activities that cannot be performed using methods known in the art. Single-cell therapy can be performed by identifying and isolating only cells exhibiting a pathology from amongst a group of many cells, treating the isolated cell in some fashion (e.g., exposure to a reagent) and returning the thus-treated cell to the original group. Groups of cells having exceptional interest include, for example, lymphocytes in blood, T jurkat cell lines, lymph node cells, tumor cells and other representative groups.

Figure 12:
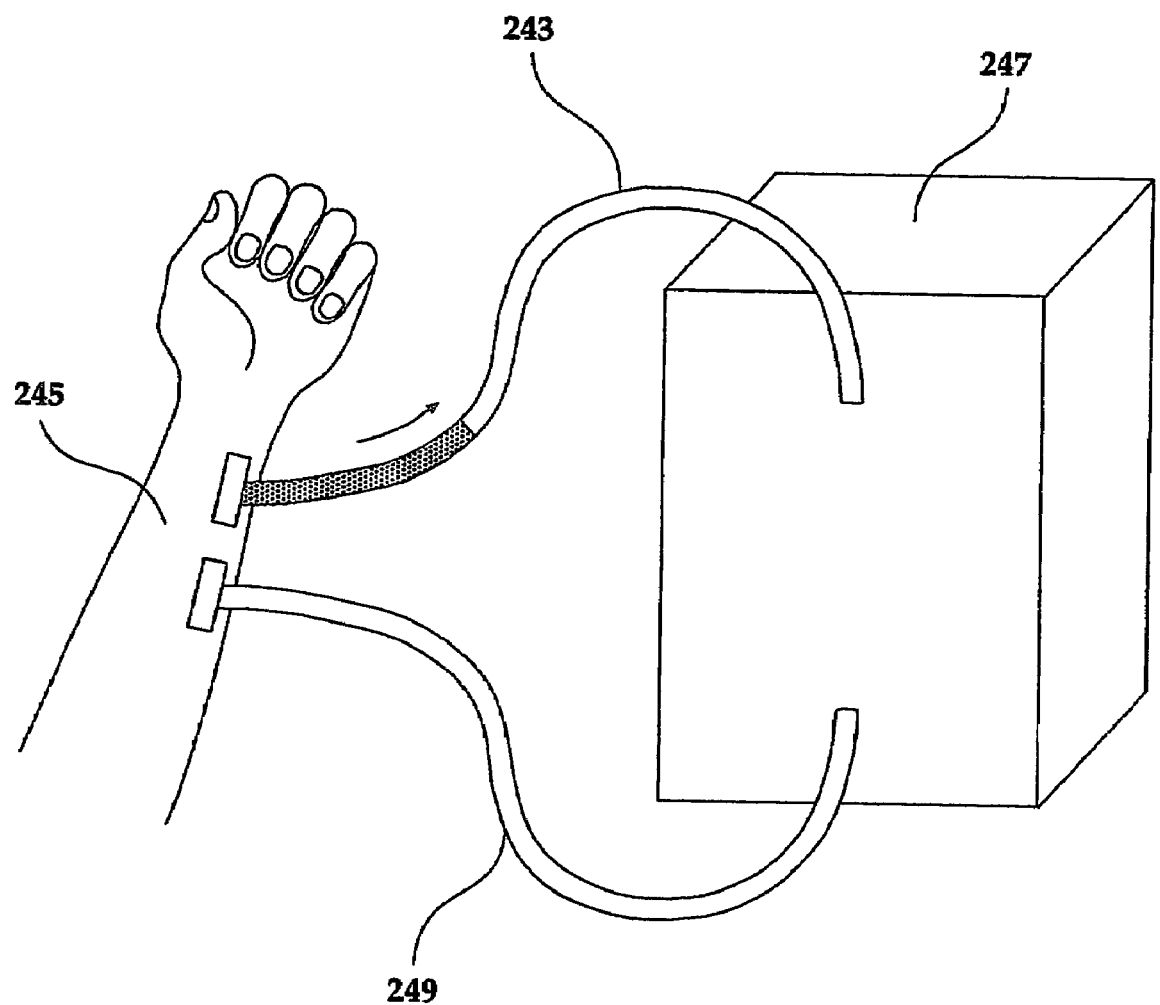
FIG. 12 is a schematic depiction of the teachings of the present invention applied to the on-line treatment of an organism.

When applied to viable cells taken from a living organism (such as a mammal, both human and non-human), the teachings of the present invention enable the treatment of biological fluids from living organisms (such as a mammal, both human and non-human) by procedures including but not limited to the manipulation of individual cells or removal of abnormal cells (especially harmful abnormal cells) from amongst normal cells. Such a treatment can be considered a form of selective manipulation of particles (especially cells) in a biological fluid, including but not limited to lymphatic fluids, blood, cerebral spinal fluids, semen, saliva, synovial fluid, bone marrow, cochlear fluid, fluid extracted from tumors, especially malignant tumors, ovarian fluid, amniotic fluid and chorionic fluid. In one embodiment, such treatments can be performed "off-line", that is by removing a sample of a biological fluid from an organism (both human and non-human) treating (e.g. selecting or manipulating cells) the fluid in a device of the present invention and returning the treated fluid to the organism. In a preferred embodiment, such treatments are performed "on-line", that is by directly attaching an input line from the organism to a device of the present invention, and returning the treated fluid to the organism. An "on-line" treatment according to the present invention of an organism is depicted in FIG. 12, where an input line 243 is attached from an organism 245 to a device of the present invention 247. In device 247 a desired treatment is performed and the treated fluid is returned from device 247 through an output line 249 back to organism 245. In such an embodiment it is advantageous that the central control unit of device 247 be configured to automatically detect and treat cells, for example by using automated image analysis.

Another experiment that is performed using the teachings of the present invention involves loading cells to be studied into trapping enclosures of cell-manipulation elements equipped with hollow penetrating-tools. The cell walls are penetrated as described hereinabove and the penetrated cell inoculated with a first reagent injected through the conduit in the hollow-penetrating tool. The thus-prepared cell is exposed to a second reagent in a manner as discussed hereinabove. The reaction of the inoculated cell is then observed.

Another related experiment involves the improved fertilization of ova (an improved form of IVF). A fluid sample containing viable ova is loaded onto a cell manipulation probe of the present invention. The ova are stored in trapping enclosures equipped with hollow penetrating tools. The walls of the ova are penetrated and sperm is injected therethrough into the ova. Each individual ovum is released from the penetrating tool but retained inside a trapping enclosure. Cell division and development is observed and only ova that are successfully fertilized and apparently viable are moved to an isolation element for transfer to a uterus.

Figure 13A:
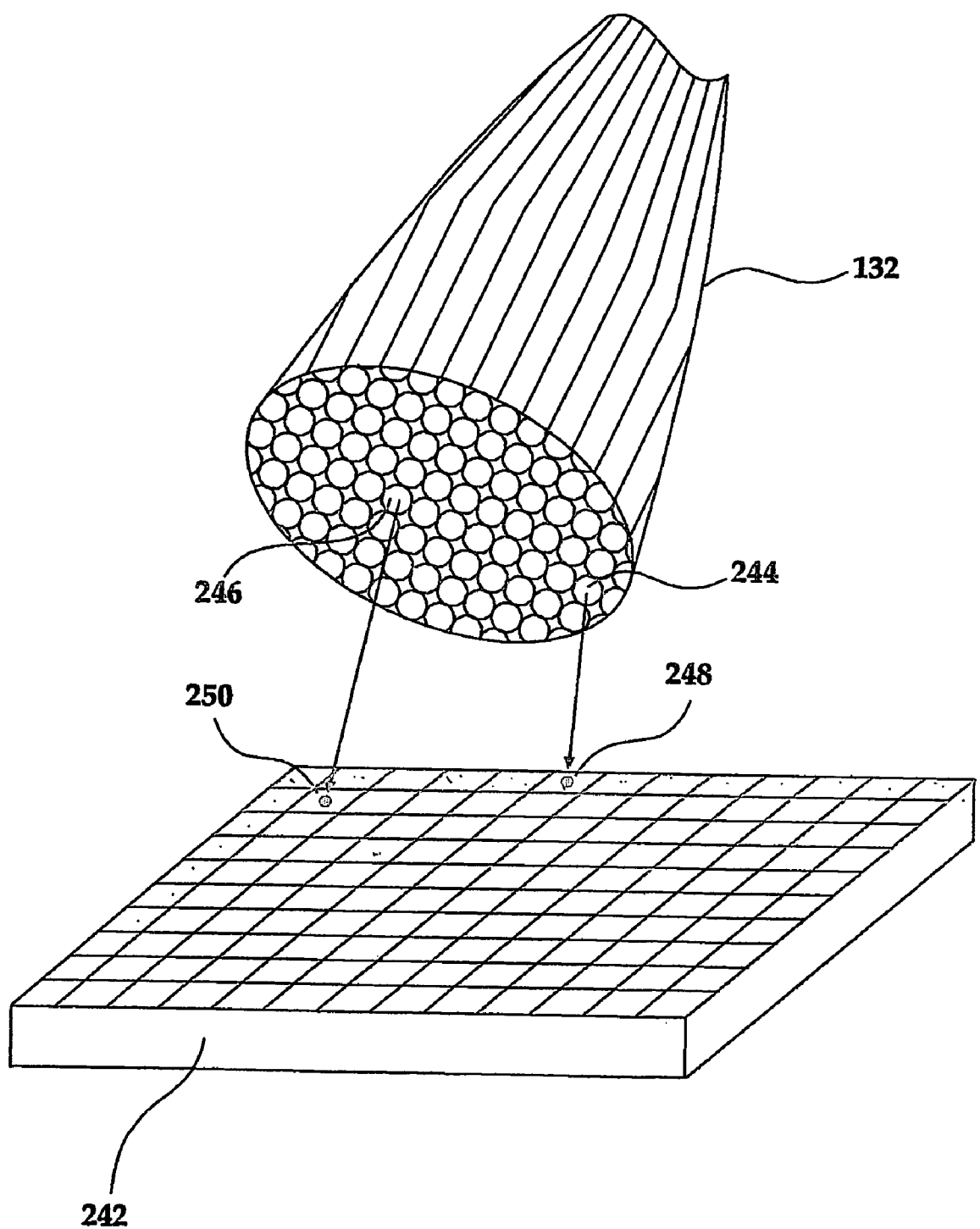
FIG. 13A is a perspective view illustrating the transfer of selected cells from a cell manipulation probe to a biochip processor.
Figure 13B:
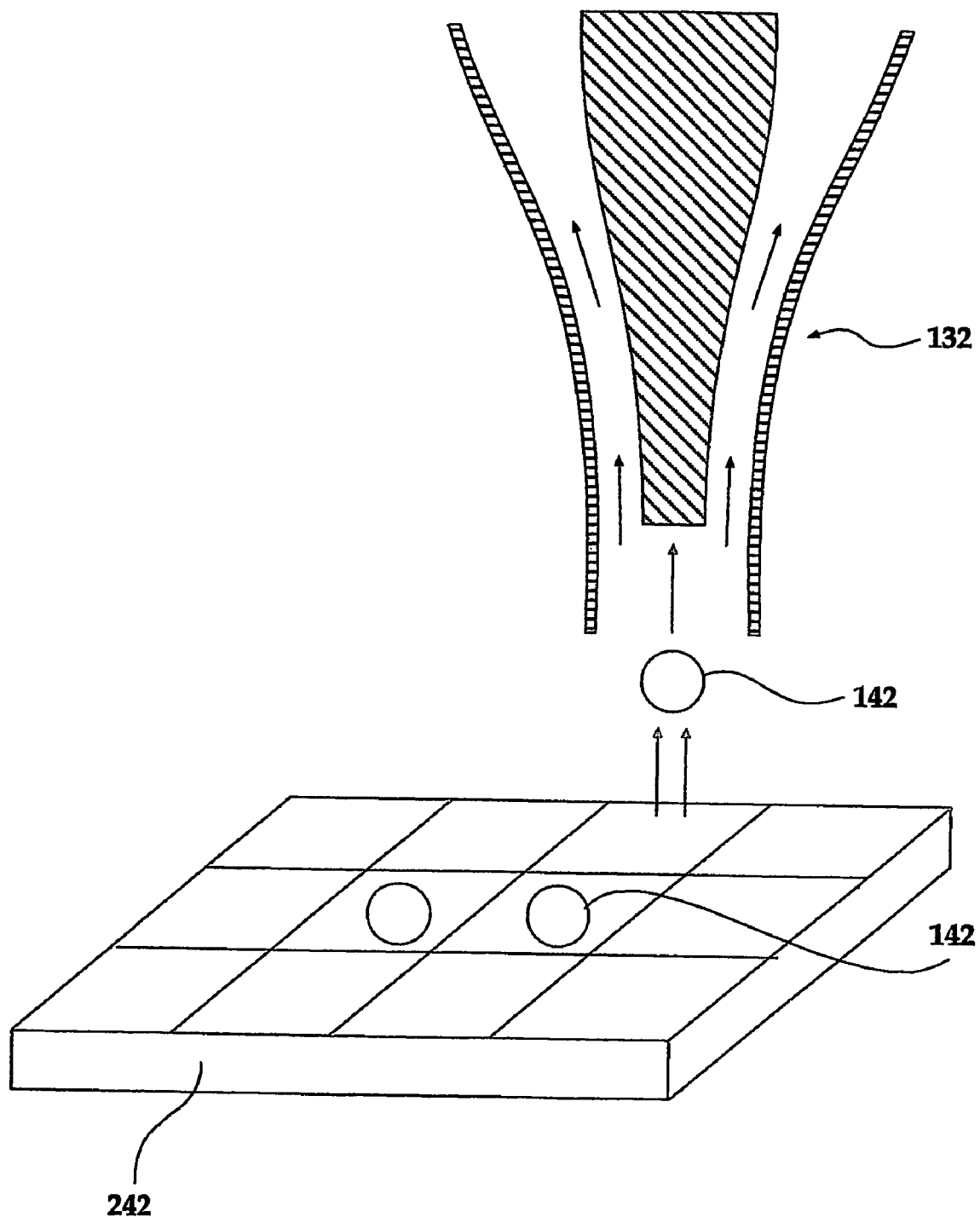
FIG. 13B is a perspective view illustrating the transfer of selected cells from a biochip processor to a cell manipulation probe.

A device of the present invention can also be used to transfer cells to a different device, for example a biochip processor as described in PCT patent application PCT2001/IL 0000992 published as WO 03/035824. Cells are loaded and undergo manipulation as described above including selection. sorting and exposure to reagents and other stimuli. When it is so desired, cell-manipulation probe 132 is brought in contact, in proximity or somehow physically connected with a fluid passage (not depicted) with the surface of biochip processor 242 (or the like such as a microwell plate such as a Nunc 384-well plate) as depicted in FIG. 13A. A specific cell or cells are deposited from chosen trapping enclosures 244 and 246 in cell-manipulation probe 132 to identifiable locations 248 and 250 on biochip processor 242. Biochip processor 242 is then used to handle the selected cells in the usual way and as described in WO 03/035824. In such a way, selected cells identified and isolated using the teachings of the present invention may be grown and allowed to proliferate. In another embodiment of the invention, this process is reversed so as to load a cell-manipulation probe 132 of the present invention with cells from a biochip processor 242 (or the like such as a microwell plate such as a Nunc 384-well plate). Cell manipulation probe 132 is brought in proximity to the surface of biochip processor 242, FIG. 13B. Associated conduit pumps are set to suction mode, loading cells 142 from biochip processor 242 to trapping enclosures of cell manipulation probe 132. The ability to easily couple two advanced research methods exponentially increases the significant results gleaned from an experiment. Such coupling is exceptionally advantageous when the two research methods are format compatible, that is, when the number, and preferably geometric arrangement, of trapping enclosures in cell manipulation probe 132 are substantially similar or even identical to the identifiable locations (such as 248 and 250) of biochip processor 242.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. For example, it is important to note that for the sake of readability, the term "pump" was used for the preferred device for the production of flow in embodiments intended for use in fluids, especially liquids. It is clear to one skilled in the art that the intent herein is rather to a flow generator, that is, a device or other means for generating a flow in a liquid.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A cell manipulation device, comprising:
   a. at least N different locations, each one of said N locations in fluid communication with and having a fixed position relative to at least one other of said N locations wherein any one said location is no more than 1000 micron distant from at least one other said location; and
   b. associated with each said location, a flow generator independently settable to a mode selected from a group of modes including a suction mode and an inactive mode
   wherein N is at least three.

2. The cell manipulation device of claim 1 wherein N is at least three and wherein at least three of said at least N locations are arranged in a 1 dimensional array.

3. The cell manipulation device of claim 1, wherein N is at least four and wherein at least four of said at least four locations are arranged in a 2 dimensional array.

4. The cell manipulation device of claim 1, wherein N is at least seven and wherein at least seven of said at least seven locations are arranged in a hexagonal lattice array.

5. The cell manipulation device of claim 1, wherein at least two of said at least N locations are substantially defined by the presence of an inlet of a respective said flow-generator.

6. The cell manipulation device of claim 1, wherein at least two of said at least N locations substantially comprise open trapping-ends of enclosures.

7. The cell manipulation device of claim 6, wherein emerging within at least two of said at least two enclosures is an inlet of a respective flow-generator.

8. The cell manipulation element of claim 6, wherein the order of the size of said at least two open trapping-ends is equal to or less than about $10^3$ micron.

9. The cell manipulation element of claim 6, wherein at least one of said N locations is associated with at least two flow generators and wherein each one of said at least two flow generators is independently settable to a mode selected from the group of modes including a suction mode and an inactive mode.

10. The cell manipulation element of claim 6, wherein at least one of said N locations is associated with at least three flow generators and wherein each one of said at least three flow generators is independently settable to a mode selected from the group of modes including a suction mode and an inactive mode.

11. The cell manipulation device of claim 1, wherein at least one of said N locations is configured to suspend a cell at distance from said at least one of said N locations using a Bernoulli effect.

12. The cell manipulation device of claim 1, wherein N is at least five and wherein at least five of said at least five locations are arranged in a rectangular lattice array.

13. The cell manipulation device of claim 1, wherein N is at least ten.

14. The cell manipulation device of claim 1, wherein N is at least 19.

15. The cell manipulation device of claim 1, wherein N is at least 24.

16. The cell manipulation device of claim 1, wherein N is at least 36.

17. The cell manipulation device of claim 5, wherein said at least two of said at least N locations are substantially depressions in a surface.

18. The cell manipulation element of claim 6, wherein the order of the size of said at least two open trapping-ends is equal to or less than about $10^2$ micron.

19. The cell manipulation element of claim 6, wherein the order of the size of said at least two open trapping-ends is equal to or less than about $10^1$ micron.

20. The cell manipulation element of claim 6, wherein the order of the size of said at least two open trapping-ends is equal to or less than about $10^0$ micron.

21. The cell manipulation device of claim 1, wherein any one said location is no more than 100 micron distant from at least one other said location.

22. The cell manipulation device of claim 1, wherein any one said location is no more than 10 micron distant from at least one other said location.

23. The cell manipulation device of claim 1, wherein any one said location is no more than 1 micron distant from at least one other said location.

* * * * *